US012733905B2

(12) United States Patent
Shimoyama

(10) Patent No.: US 12,733,905 B2
(45) Date of Patent: Sep. 15, 2026

(54) DETACHABLE ULTRASONIC WAVE TRANSMISSION MEDIUM SUPPLY/DISCHARGE MEMBER AND ENDOSCOPE SYSTEM

(71) Applicant: FUJIFILM Corporation, Tokyo (JP)

(72) Inventor: Yuto Shimoyama, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 58 days.

(21) Appl. No.: 18/596,663

(22) Filed: Mar. 6, 2024

(65) Prior Publication Data

US 2024/0307034 A1 Sep. 19, 2024

(30) Foreign Application Priority Data

Mar. 13, 2023 (JP) ................................ 2023-038759
Feb. 19, 2024 (JP) ................................ 2024-023162

(51) Int. Cl.
*A61B 8/00* (2006.01)
*A61B 8/12* (2006.01)
*A61M 25/10* (2013.01)

(52) U.S. Cl.
CPC .............. *A61B 8/4281* (2013.01); *A61B 8/12* (2013.01); *A61B 8/445* (2013.01); *A61M 2025/1061* (2013.01)

(58) Field of Classification Search
CPC ............................................ A61M 2025/1061
See application file for complete search history.

(56) References Cited

U.S. PATENT DOCUMENTS

| | | | | |
|---|---|---|---|---|
| 2011/0034768 A1* | 2/2011 | Ozaki | A61B 1/00167 600/109 |
| 2021/0177243 A1* | 6/2021 | Hamada | A61B 1/0011 |
| 2021/0338066 A1* | 11/2021 | Tsuruta | A61B 8/483 |

FOREIGN PATENT DOCUMENTS

| | | |
|---|---|---|
| JP | 2019068931 | 5/2019 |

* cited by examiner

*Primary Examiner* — Keith M Raymond
*Assistant Examiner* — Ashish S. Jasani
(74) *Attorney, Agent, or Firm* — JCIPRNET

(57) ABSTRACT

An ultrasonic wave transmission medium supply/discharge member includes a balloon for an ultrasonic endoscope that is mounted to cover an outer surface of an ultrasound transducer provided in a distal end part body on a distal end side of an insertion portion of an ultrasonic endoscope, in which the balloon for an ultrasonic endoscope has a storage portion that is configured to be filled with an ultrasonic wave transmission medium, a tube that communicates with an inside of the storage portion, and a fixing portion that is configured to be attachably and detachably fixed to an operating portion of the ultrasonic endoscope and that is connected to the balloon for an ultrasonic endoscope through the tube.

16 Claims, 25 Drawing Sheets

Z(−)
X
Y(+)
Y(−)
Z(+)
122
52
34
93
122q
121b
120
124
124f
1100B
92
91
93
34
50
51
122
122a
122q
120
124
124f
1100A 34
120
56
58
23
40
40c
40b
84
40a
85
74
52
140
122
122k
122e
94
50
124f
124d
122d
124g
121
124
X
Y(+)
Y(−)
Z(+)
Z(−)

DETACHABLE ULTRASONIC WAVE TRANSMISSION MEDIUM SUPPLY/DISCHARGE MEMBER AND ENDOSCOPE SYSTEM

CROSS-REFERENCE TO RELATED APPLICATION

The present application claims priorities under 35 U.S.C § 119(a) to Japanese Patent Application No. 2023-038759 filed on Mar. 13, 2023 and Japanese Patent Application No. 2024-023162 filed on Feb. 19, 2024, each of which is hereby expressly incorporated by reference, in its entirety, into the present application.

BACKGROUND OF THE INVENTION

1. Field of the Invention

The present invention relates to an ultrasonic wave transmission medium supply/discharge member and an endoscope system, and in particular, relates to an ultrasonic wave transmission medium supply/discharge member comprising a balloon for an ultrasonic endoscope that is mounted on a distal end part body of an insertion portion of an ultrasonic endoscope and an endoscope system.

2. Description of the Related Art

In the medical field, an ultrasonic endoscope is used. The ultrasonic endoscope disposes an imaging element and an ultrasound transducer integrally in a distal end part of an insertion portion that is inserted into a body cavity of a subject. The ultrasound transducer emits an ultrasonic wave toward a site to be observed in the body cavity and receives an echo signal reflected from the site to be observed, and an electric signal depending on the received echo signal is output to an ultrasonic observation device. Then, the electric signal is subjected to various kinds of signal processing in the ultrasonic observation device, and is then displayed as an ultrasound tomographic image on a monitor or the like.

The ultrasonic wave and the echo signal are considerably attenuated in air. For this reason, there is a need to interpose an ultrasonic wave transmission medium, such as water or oil, between the ultrasound transducer and the site to be observed. Accordingly, an expandable balloon (balloon for an ultrasonic endoscope) is mounted on a distal end part of an ultrasonic endoscope, and the ultrasonic wave transmission medium is injected into the balloon to expand the balloon to be brought into contact with the site to be observed. As a result, air is eliminated from a region between the ultrasound transducer and the site to be observed, and the attenuation of the ultrasonic wave and of the echo signal is restrained.

As the balloon that is mounted on the distal end part of the insertion portion, various balloons have been suggested. For example, JP2019-068931A discloses a technique in which an ultrasonic wave transmission medium is stored between an oscillator and a balloon, a distal end part of an insertion portion comprises a protrusion or a locking groove for mounting the balloon, and the balloon comprises a locking ring that is fitted into the locking groove.

SUMMARY OF THE INVENTION

In JP2019-068931A, a tube for supplying and discharging an ultrasonic wave transmission medium to and from a balloon is provided inside an insertion portion, but in a case where the tube is provided outside the insertion portion, there is an advantage in that a diameter of the insertion portion can be reduced. In this case, a distal end side of the tube communicates with an ultrasonic wave transmission medium storage portion (hereinafter, referred to as a "storage portion") in the balloon, and a supply/discharge unit such as a syringe is connected to a proximal end side of the tube.

However, in the above-described configuration, since the tube may be routed during an operation of an ultrasonic endoscope by a practitioner, there is a problem in that an operability of the ultrasonic endoscope is hindered.

The present invention has been made in view of such circumstances, and an object of the present invention is to provide an ultrasonic wave transmission medium supply/discharge member and an endoscope system capable of improving operability of an ultrasonic endoscope.

In order to achieve the above object, the present invention is formed in the following aspects.

An ultrasonic wave transmission medium supply/discharge member according to a first aspect comprises a balloon for an ultrasonic endoscope that is mounted to cover an outer surface of an ultrasound transducer provided in a distal end part body on a distal end side of an insertion portion of an ultrasonic endoscope, in which the balloon for an ultrasonic endoscope has a storage portion that is configured to be filled with an ultrasonic wave transmission medium, a tube that communicates with an inside of the storage portion, and a fixing portion that is configured to be attachably and detachably fixed to an operating portion of the ultrasonic endoscope and that is connected to the balloon for an ultrasonic endoscope through the tube.

A second aspect provides the ultrasonic wave transmission medium supply/discharge member according to the first aspect, in which the fixing portion has an operation member that operates to hold and release a fixed state of the fixing portion to the operating portion.

A third aspect provides the ultrasonic wave transmission medium supply/discharge member according to the first or second aspect, in which the fixing portion has a port portion that supplies and discharges the ultrasonic wave transmission medium to and from the tube.

A fourth aspect provides the ultrasonic wave transmission medium supply/discharge member according to the third aspect, in which the port portion has a supply/discharge port to which a supply/discharge unit for supplying and discharging the ultrasonic wave transmission medium is connectable.

A fifth aspect provides the ultrasonic wave transmission medium supply/discharge member according to the fourth aspect, in which the supply/discharge port has a shape that is connectable with a luer lock connector.

A sixth aspect provides the ultrasonic wave transmission medium supply/discharge member according to the fourth or fifth aspect, in which the supply/discharge port is configured to supply and discharge the ultrasonic wave transmission medium through a luer lock connector.

A seventh aspect provides the ultrasonic wave transmission medium supply/discharge member according to any one of the first to sixth aspects, in which the fixing portion has a pair of grip bodies facing each other, and a connecting member that rotatably connects the pair of grip bodies to each other.

An eighth aspect provides the ultrasonic wave transmission medium supply/discharge member according to the seventh aspect, in which the connecting member has a port portion that supplies and discharges the ultrasonic wave transmission medium to and from the tube.

A ninth aspect provides the ultrasonic wave transmission medium supply/discharge member according to the eighth aspect, in which the port portion has a structure that is attachable to and detachable from the connecting member.

A tenth aspect provides the ultrasonic wave transmission medium supply/discharge member according to any one of the seventh to ninth aspects, in which the fixing portion has a grip force applying member that applies grip force of the pair of grip bodies.

An eleventh aspect provides the ultrasonic wave transmission medium supply/discharge member according to any one of the first to tenth aspects, in which the fixing portion has a shape that avoids a protrusion portion included in the operating portion.

A twelfth aspect provides the ultrasonic wave transmission medium supply/discharge member according to the eleventh aspect, in which the fixing portion has a shape that is engageable with a shape of the protrusion portion.

A thirteenth aspect provides the ultrasonic wave transmission medium supply/discharge member according to the eleventh or twelfth aspect, in which the protrusion portion is a forceps introduction portion of a forceps sleeve provided in the operating portion.

A fourteenth aspect provides the ultrasonic wave transmission medium supply/discharge member according to any one of the first to thirteenth aspects, in which the fixing portion has an anti-slip member at a portion that comes into contact with the operating portion.

An endoscope system according to a fifteenth aspect comprises the ultrasonic wave transmission medium supply/discharge member according to any one of the first to fourteenth aspects; and an ultrasonic endoscope including an operating portion that is configured to be attachably and detachably fixed to the fixing portion.

A sixteenth aspect provides the endoscope system according to the fifteenth aspect, in which the operating portion has a protrusion portion that is engageable with the fixing portion.

A seventeenth aspect provides the endoscope system according to the sixteenth aspect, in which the protrusion portion is a forceps introduction portion of a forceps sleeve provided in the operating portion.

According to the present invention, it is possible to improve the operability of the ultrasonic endoscope.

DESCRIPTION OF THE PREFERRED EMBODIMENTS

Hereinafter, an embodiment of the present invention will be described in accordance with the accompanying drawings. An endoscope system (an example of an endoscope system of the embodiment of the present invention) according to the present embodiment is configured to comprise an ultrasonic endoscope 1 and an ultrasonic wave transmission medium supply/discharge member 150, which will be described later. Hereinafter, the configuration of the ultrasonic endoscope 1 will be described, and then, the configuration of the ultrasonic wave transmission medium supply/discharge member 150 will be described.

Overall Configuration of Ultrasonic Endoscope

Figure 1:
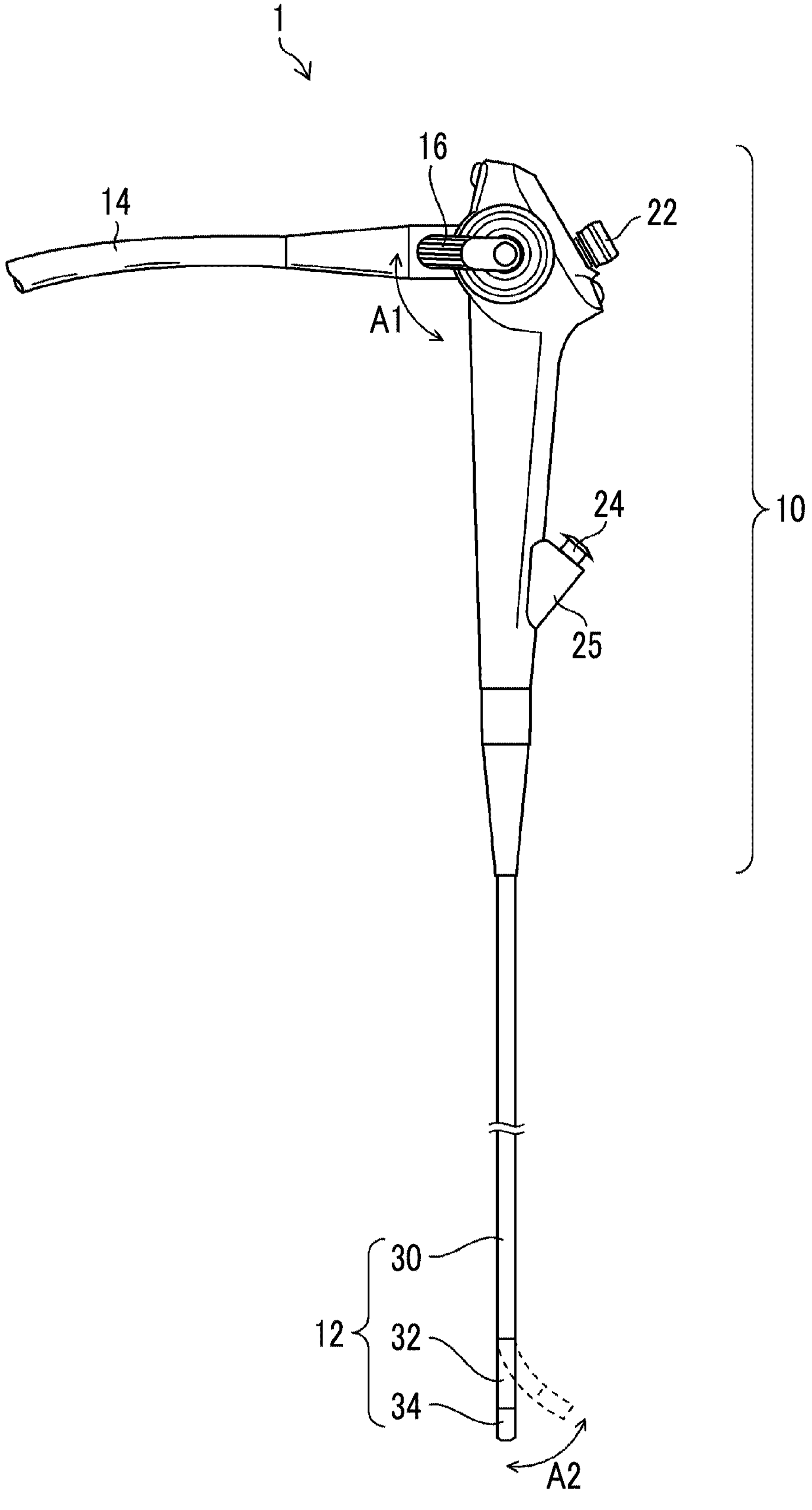
FIG. 1 is a general view of an ultrasonic endoscope.

FIG. 1 is a general view of the ultrasonic endoscope 1. As shown in FIG. 1, the ultrasonic endoscope 1 (hereinafter, simply referred to as an "endoscope 1") is an example of an ultrasonic endoscope of the embodiment of the present invention and is used for collection or the like of a cellular tissue of a lesion part (an observation part, a test part, or an examination part can be used). In the present embodiment, description will be provided in connection with a lymph node of a bronchus as an example of a lesion part.

The endoscope 1 comprises an operating portion 10 that is gripped by a practitioner and that is used for various operations, an insertion portion 12 that is inserted into a body of a patient, and a universal cord 14. The endoscope 1 is connected to system constituent devices that configure an endoscope system, such as a processor device, a light source device, and an ultrasonic observation device (not shown), through the universal cord 14.

The operating portion 10 is provided with various operation members that are operated by the practitioner. For example, an angle lever 16, a suction button 22, and the like are provided.

The operating portion 10 is provided with a treatment tool inlet port 24 through which a treatment tool is inserted into a treatment tool insertion channel 23 (see FIG. 3) that is inserted into the insertion portion 12.

The insertion portion 12 extends from a distal end of the operating portion 10 and is formed in a small-diameter elongated shape as a whole. The insertion portion 12 is configured by a soft part 30, a bendable part 32, and a distal end part body 34 in order from a proximal end side to a distal end side.

The soft part 30 occupies most of the insertion portion 12 from the proximal end side and has enough flexibility to be bent in any direction. In a case where the insertion portion 12 is inserted into a body cavity, the soft part 30 is bent along an insertion path into the body cavity.

The bendable part 32 is bent in an up-down direction (A2 direction) by rotating the angle lever 16 of the operating portion 10 in an A1 direction. With the bending operation of the bendable part 32, the distal end part body 34 can be directed in a desired direction.

As will be described with reference to FIGS. 2 and 3 in detail below, the distal end part body 34 comprises an observation optical system 40 and illumination optical systems 44 that are provided to capture an observation image in a body, an ultrasound transducer 50 that acquires an ultrasound image, and a treatment tool outlet port 52 (hereinafter, referred to as an outlet port 52) from which the treatment tool inserted from the treatment tool inlet port 24 is led out.

The universal cord 14 includes a signal cable 54, a signal cable 56, and light guides 58 shown in FIG. 3 described below in detail. A connector is provided in an end portion (not shown) of the universal cord 14. The connector is connected to predetermined system constituent devices that configure the endoscope system, such as a processor device, a light source device, and an ultrasonic observation device. As a result, power, control signals, illumination light, and the like necessary for the operation of the endoscope 1 are supplied from the system constituent devices to the endoscope 1. A signal of the observation image acquired by the observation optical system 40 and a signal of the ultrasound image acquired by the ultrasound transducer 50 are transmitted from the endoscope 1 to the system constituent devices. The signals transmitted to the system constituent devices are subjected to image processing, the observation image and the ultrasound image are displayed on a monitor, and the practitioner or the like can observe the images.

The configuration of the operating portion 10 is not limited to the aspect shown in FIG. 1. A pair of angle knobs may be provided instead of the angle lever 16, and the bendable part 32 may be bent in the up-down direction and in a right-left direction by rotating the pair of angle knobs. An air/water supply button may be provided in the operating portion 10, and gas, such as air, a liquid for cleaning, or the like may be supplied to the distal end part body 34 by operating the air/water supply button.

Configuration of Distal End Part Body

Figure 2:
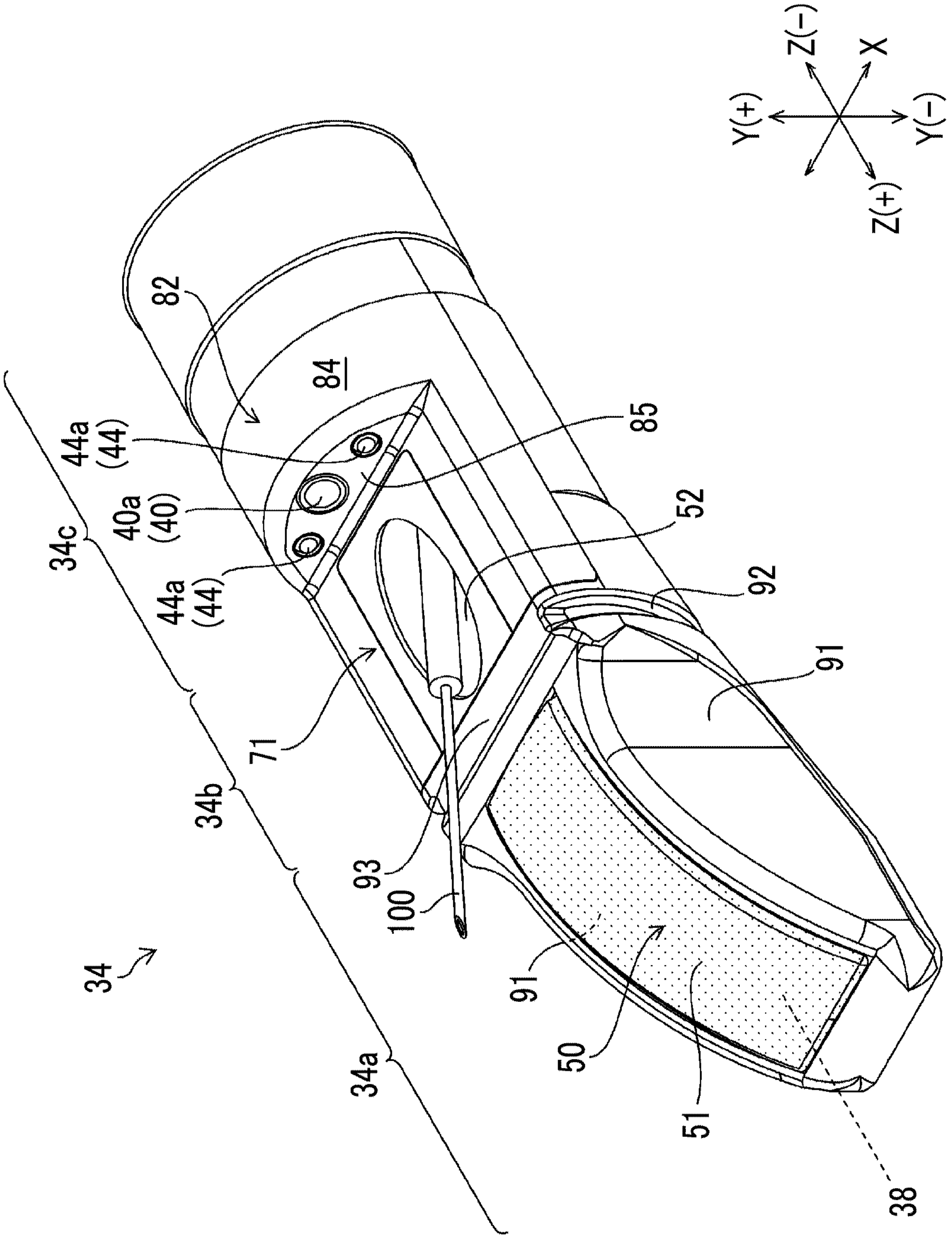
FIG. 2 is a perspective view of a distal end part body.

FIG. 2 is a perspective view of the distal end part body 34 from which a puncture needle 100 is led out. FIG. 3 is a sectional view of the distal end part body 34.

Hereinafter, in describing the configuration of each part, a three-dimensional rectangular coordinate system of an X axis, a Y axis, and a Z axis is used. A Z direction in the drawings is a direction parallel to a longitudinal axis 38 of the distal end part body 34 (insertion portion 12). A Z(+) direction side of the Z direction in the drawings is a distal end side of the distal end part body 34, and a Z(−) direction side is a proximal end side of the distal end part body 34. A Y direction in the drawings is perpendicular to the Z direction and is an up-down direction in each drawing in the present embodiment. A Y(+) direction side as one direction side of the Y direction is an up direction in the drawings, and a Y(−) direction side as the other direction side opposite to the one direction side of the Y direction is a down direction in the drawings. An X direction in the drawings is a direction perpendicular to both the Z direction and the Y direction.

Figure 3:
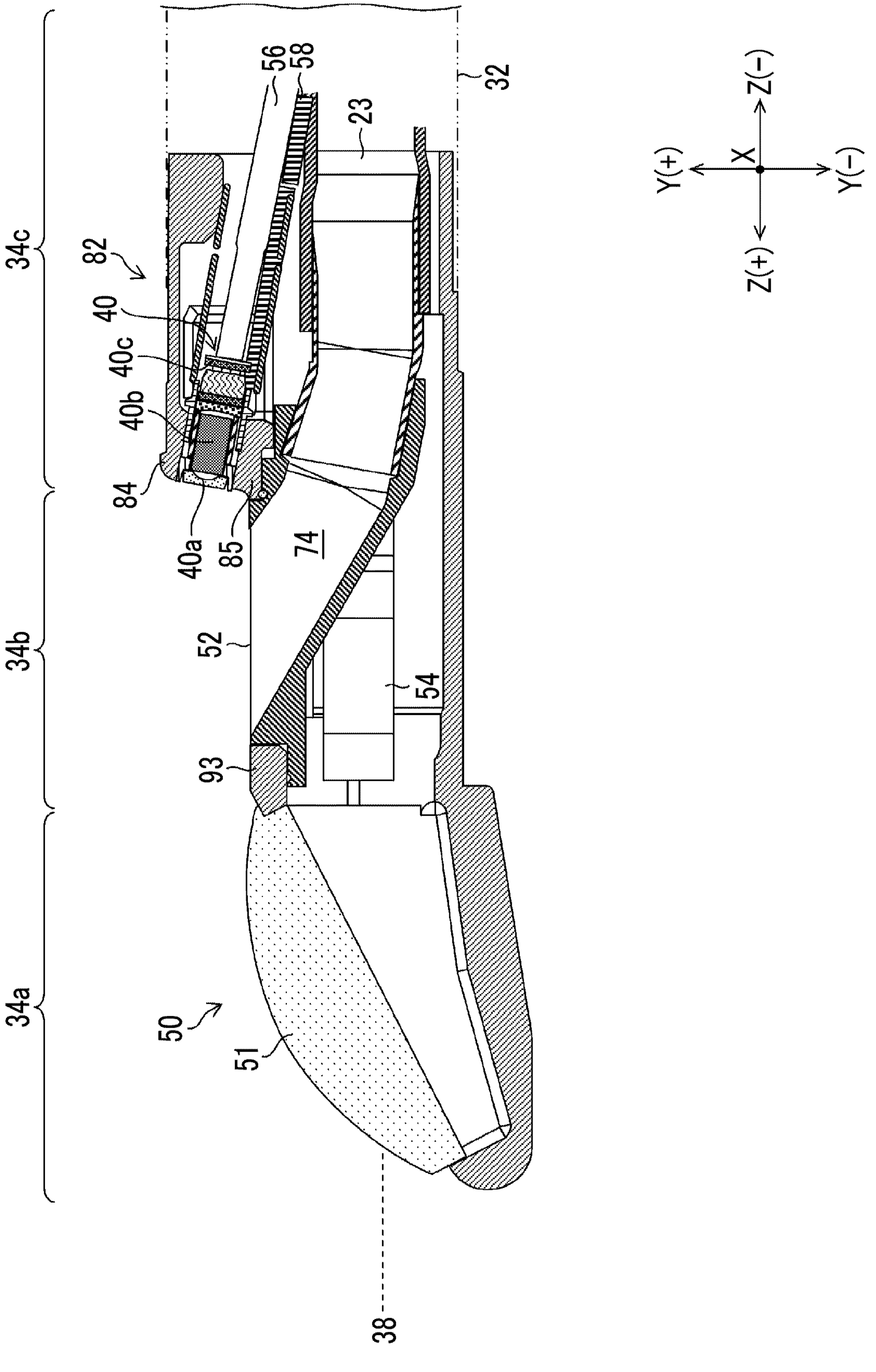
FIG. 3 is a sectional view of the distal end part body.

As shown in FIGS. 2 and 3, the distal end part body 34 comprises, from the distal end side toward the proximal end side of the distal end part body 34, an ultrasonic attachment portion 34*a*, an outlet port forming portion 34*b*, and a body portion 34*c*.

The ultrasound transducer 50 is attached to the ultrasonic attachment portion 34*a* in a posture tilted forward (inclined) to the Y(−) direction side with respect to the longitudinal axis 38 in a case where the distal end part body 34 is viewed from the X direction side. The ultrasound transducer 50 is a convex type that has an oscillator surface 51 on which ultrasound oscillators that transmit and receive ultrasonic waves are arranged in an arc shape along a direction of the longitudinal axis 38. The ultrasound transducer 50 transmits ultrasonic waves from the oscillator surface 51 toward a living body and receives an ultrasound echo reflected by a living body tissue on the oscillator surface 51. A signal that generates an ultrasound image of a lymph node is acquired by the ultrasound transducer 50. The number of ultrasound oscillators that configure the ultrasound transducer 50 is not limited.

The outlet port forming portion 34*b* has an outlet port 52 for a treatment tool that is opened on the Y(+) direction side, and a substantially rectangular opening forming surface 71 parallel to an XZ plane in which the outlet port 52 is opened and along the Z direction (including the longitudinal axis 38; the same applies hereinafter). The opening forming surface 71 is a surface parallel to the XZ plane and along the Z direction, and configures a part of an outer peripheral surface of the distal end part body 34. In the present embodiment, although the outlet port 52 is opened in the planar opening forming surface 71, the outlet port 52 may be opened in surfaces of various shapes, such as a curved surface, an inclined surface, or an uneven surface. In the present embodiment, description will be provided in connection with a puncture needle 100 that is used in tissue sampling, such as a lymph node, as an example of the treatment tool.

A pipe line 74 is formed inside the outlet port forming portion 34*b* and the body portion 34*c*. A distal end side of the pipe line 74 is connected to the outlet port 52, and a proximal end side of the pipe line 74 is connected to the treatment tool insertion channel 23 inserted into the insertion portion 12. As a result, a distal end of the puncture needle 100 inserted from the treatment tool inlet port 24 is guided to the outlet port 52 by way of the treatment tool insertion channel 23 and the pipe line 74, and is led out from the outlet port 52 to the outside.

The body portion 34*c* comprises an optical system storage portion 82 in which the observation optical system 40 and the illumination optical systems 44 are disposed. The optical system storage portion 82 has a substantially semi-cylindrical shape, and has a convex surface 84 and a stepped surface 85. The convex surface 84 configures a part of the outer peripheral surface of the distal end part body 34 (optical system storage portion 82). The convex surface 84 is positioned on the Y(+) direction side with respect to the opening forming surface 71 and has a shape along the Z direction. The convex surface 84 may be formed in various shapes, such as a curved surface, an inclined surface, or an uneven surface.

The stepped surface 85 is an inclined surface that connects a proximal end side of the opening forming surface 71 and a distal end side of the convex surface 84, and configures a part of the outer peripheral surface of the distal end part body 34. The inclined surface used herein includes a vertical surface having an inclined angle of 90° with respect to the Z direction.

The stepped surface 85 is provided with an observation window 40*a* of the observation optical system 40 and illumination windows 44*a* of a pair of illumination optical systems 44.

The observation optical system 40 includes the observation window 40*a* provided in the stepped surface 85, and a lens system 40*b* and an imaging element 40*c* provided in the optical system storage portion 82. The imaging element 40*c* is a charge-coupled device (CCD) type or a complementary metal-oxide-semiconductor (CMOS) type image sensor and captures an observation image taken from the observation window 40*a* through the lens system 40*b*. Then, the imaging element 40*c* outputs an imaging signal of the observation image to the system constituent devices through the signal cable 56 inserted into the insertion portion 12.

The illumination optical systems 44 are provided on both sides of the observation optical system 40 in the X direction, and the illumination optical systems 44 include the illumination window 44*a* provided in the stepped surface 85, and the light guide 58 inserted into the insertion portion 12. An emission end of the light guide 58 is disposed rearward of each illumination window 44*a*. As a result, illumination light supplied from the light source device to each light guide 58 is emitted from each illumination window 44*a*.

As described above, in the distal end part body 34, the ultrasound transducer 50, the outlet port 52, and the stepped surface 85 (observation window 40*a*) are disposed in order from the distal end side toward the proximal end side. That is, the outlet port 52 is disposed between the ultrasound transducer 50 and the observation window 40*a*. For this reason, a puncture site toward a lymph node in a bronchial wall surface by the puncture needle 100 can be observed with the observation optical system 40.

Figure 4:
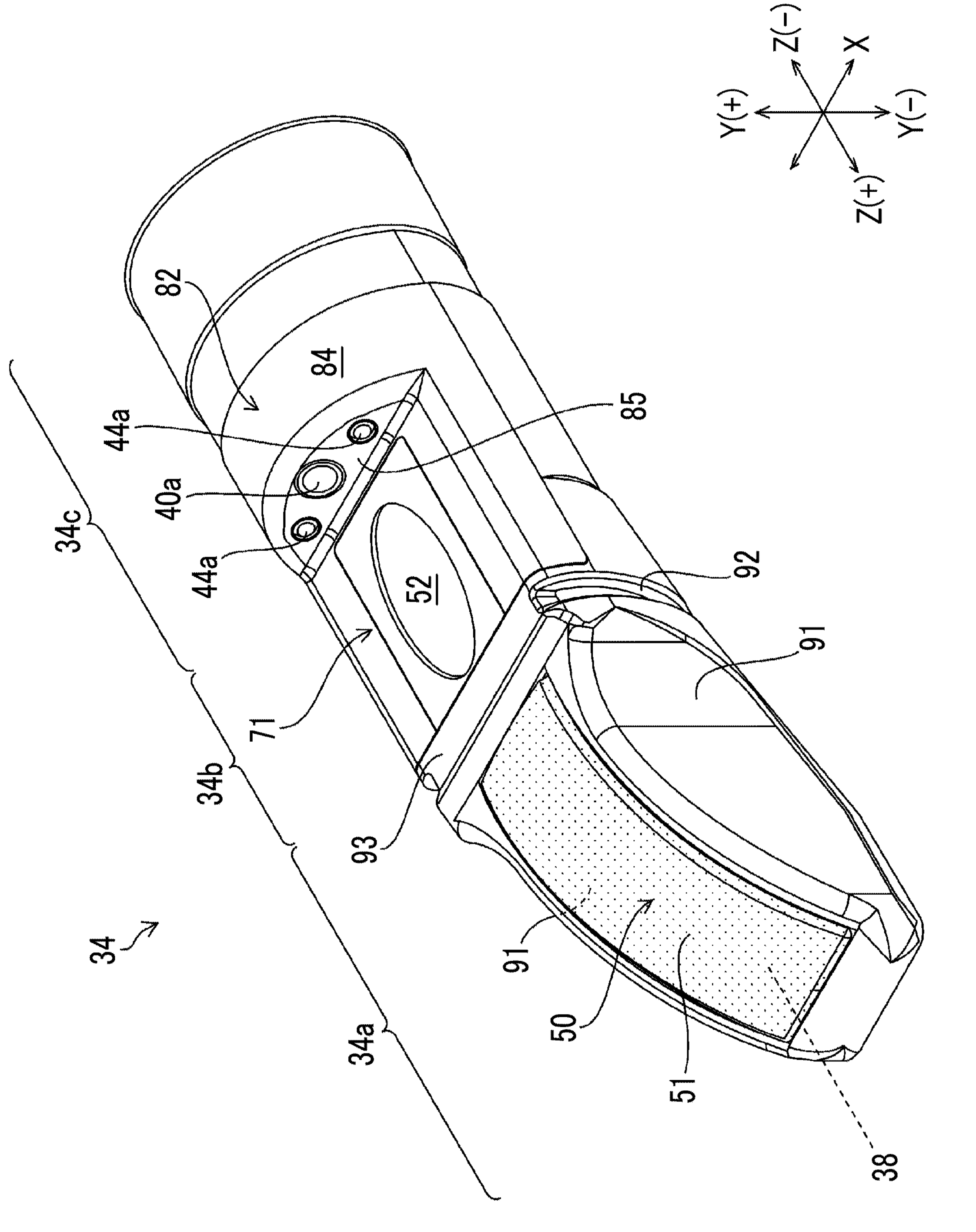
FIG. 4 is a perspective view of the distal end part body.
Figure 5:
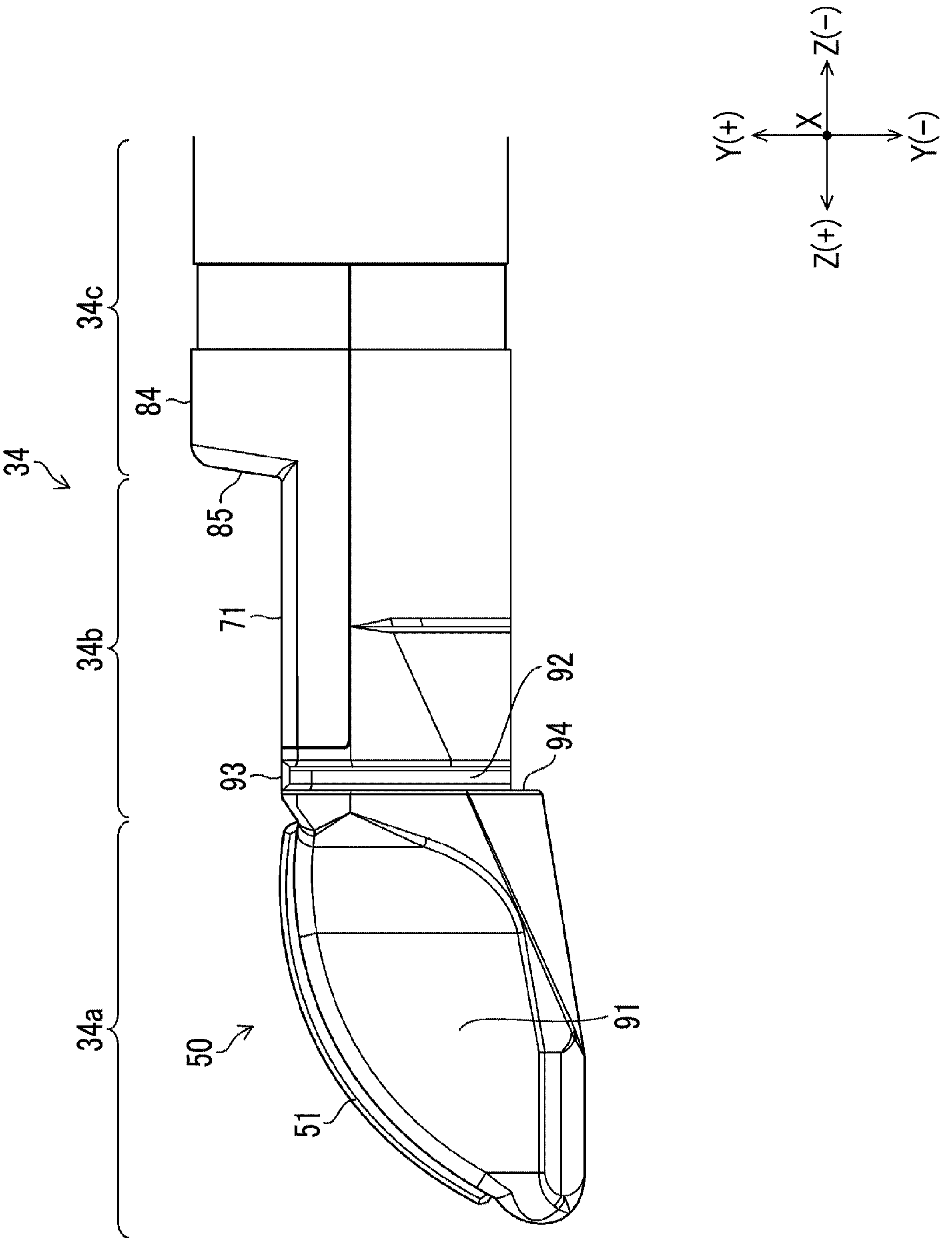
FIG. 5 is a side view of the distal end part body.
Figure 6:
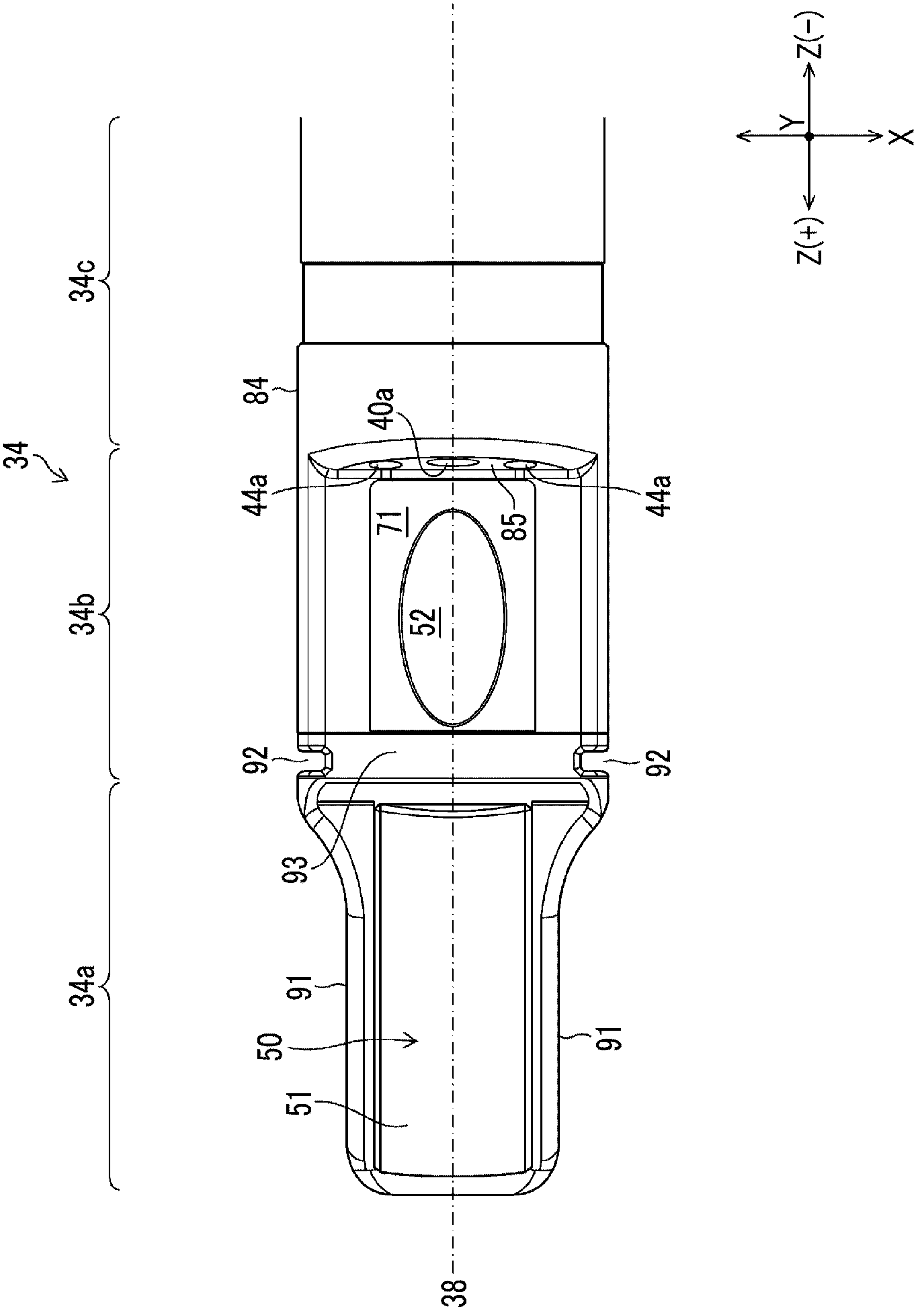
FIG. 6 is a plan view of the distal end part body.

Next, the configuration of the distal end part body 34 on which a balloon 120 described below is mounted will be described. FIG. 4 is a perspective view of the distal end part body 34. FIG. 5 is a side view of the distal end part body 34. FIG. 6 is a plan view of the distal end part body 34.

The distal end part body 34 has standing wall portions 91 on both side surfaces of the ultrasound transducer 50 in a width direction (X direction) that is a direction perpendicular to the Z direction and that is a direction parallel to a plane direction of the oscillator surface 51 of the ultrasound transducer 50. The two standing wall portions 91 are configured with surfaces parallel to a YZ plane. The standing wall portions 91 do not need to be parallel to the YZ plane over the entire surface, and parallel can mean substantially parallel. A distance between the two standing wall portions 91 in the width direction, that is, a width of the ultrasonic attachment portion 34*a*, is shorter than other portions (the outlet port forming portion 34*b* and the body portion 34*c*) of the distal end part body 34 in a case of being viewed from the Y direction (see FIG. 6).

Fixing portions of the balloon 120 described below are in close contact with and fixed to the standing wall portions 91, whereby the balloon is fixed to the distal end part body 34.

The distal end part body 34 has a plane portion 93 between the ultrasound transducer 50 and the outlet port 52. The plane portion 93 is a plane substantially parallel to the XZ plane and has a length in the X direction longer than a length in the Z direction. The plane portion 93 is connected on the proximal end side of the above-described two standing wall portions 91, and the plane portion 93 and the opening forming surface 71 configure an integrated plane.

The distal end part body 34 has groove portions 92 on each of both side surfaces of the distal end part body 34 in the X direction between the ultrasound transducer 50 and the outlet port 52. In other words, as shown in FIG. 6, in a case where the distal end part body 34 is viewed from the Y(+) direction side, the groove portions 92 are disposed between the ultrasound transducer 50 and the outlet port 52. The groove portions 92 extend from both end portions of the plane portion 93 to be parallel to the Y direction on the Y(−) direction side (see FIG. 5) and are disposed on both sides of the plane portion 93 (see FIG. 6). That is, the groove portions 92 are disposed on a proximal end side (Z(−) direction side) of the ultrasound transducer 50 and are disposed on both sides of the ultrasound transducer 50 in a case where the distal end part body 34 is viewed from the Z(+) direction side. In FIGS. 4 to 6, although the groove portions 92 are provided on the proximal end side of the ultrasound transducer 50, positions where the groove portions 92 are formed are not limited to the proximal end side of the ultrasound transducer 50, and may be provided in the standing wall portions 91.

As described below, protrusion portions 122*j* that are provided in a fixing portion of the balloon 120 are fitted into the groove portions 92. Since the groove portions 92 and the protrusion portions 122*j* are fitted, it can be made difficult for the balloon 120 to fall off from the distal end part body 34.

The distal end part body 34 has a stepped portion 94 on a surface on an opposite side to the oscillator surface 51 on the proximal end side (Z(−) direction side) of the ultrasound transducer 50 (see FIG. 5). The stepped portion 94 is a plane substantially parallel to the XY plane and protrudes in the Y(−) direction as viewed from the Z(−) direction side.

As described below, the stepped portion 94 is locked to a locking portion 122*k* that is provided in the fixing portion of the balloon 120, whereby it is possible to prevent the balloon 120 from falling off from the distal end part body 34.

Configuration of Balloon

Next, the balloon 120 of the embodiment will be described. In the drawings, similarly to FIGS. 2 to 6, description will be provided using the three-dimensional rectangular coordinate system of the X axis, the Y axis, and the Z axis. The X axis, the Y axis, and the Z axis coincide with the X direction, the Y direction, and the Z direction in a case where the balloon 120 is mounted on the distal end part body 34. A Z(+) direction side is a distal end side, and a Z(−) direction side is a proximal end side. A Z direction in the drawings is a direction parallel to a longitudinal axis 38 of the distal end part body 34 (insertion portion 12). A Y direction in the drawings is perpendicular to the Z direction and is an up-down direction in each drawing in the present embodiment. A Y(+) direction side as one direction side of the Y direction is an up direction in the drawings, and a Y(−) direction side as the other direction side opposite to the one direction side of the Y direction is a down direction in the drawings. An X direction in the drawings is a direction perpendicular to both the Z direction and the Y direction.

Figure 7:
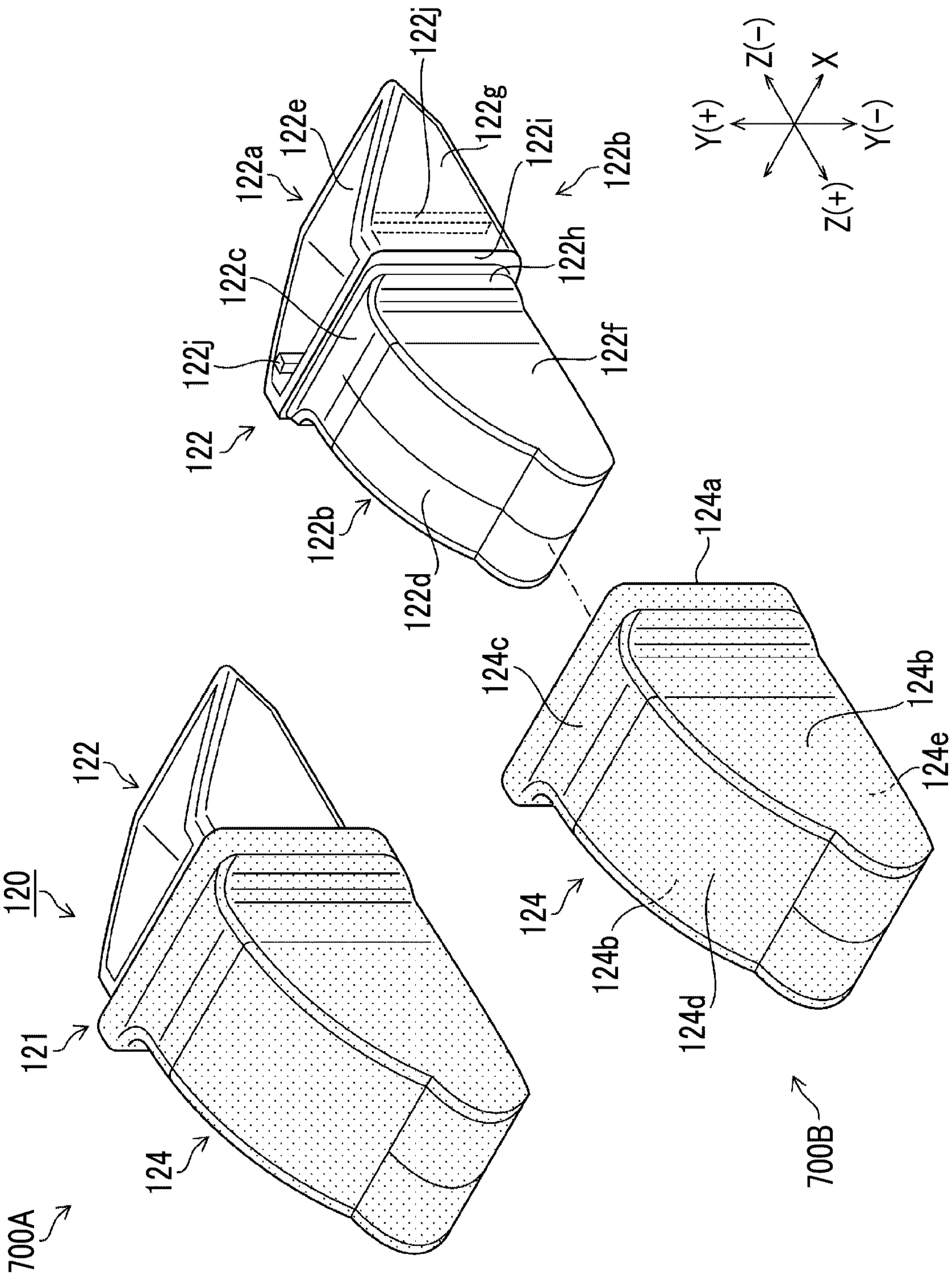
FIG. 7 is an exploded assembly diagram of a balloon for an ultrasonic endoscope in which a tube is omitted.

FIG. 7 is an assembly diagram of the balloon 120 in which a tube 140 described below is omitted, 700A of FIG. 7 is a perspective view after assembly, and 700B of FIG. 7 is a perspective view before assembly. As shown in FIG. 7, the balloon 120 is configured with a balloon body 121 of a two-layer structure including an inner portion 122 and an outer portion 124.

Inner Portion

The inner portion 122 has an opening portion 122*a* at one end in the Z direction, and comprises two side surface portions 122*b* disposed to face each other, a top surface portion 122*c*, an inclined surface portion 122*d*, and a bottom surface portion 122*e*. The inner portion 122 is configured in a bottomed tubular shape having the opening portion 122*a*, and portions other than the opening portion 122*a* are closed by the two side surface portions 122*b*, the top surface portion 122*c*, the inclined surface portion 122*d*, and the bottom surface portion 122*e*.

Each side of the two side surface portions 122*b*, the top surface portion 122*c*, and the bottom surface portion 122*e* that define the opening portion 122*a* is linear, and a shape of the opening portion 122*a* is a substantially rectangular shape.

The opening portion 122*a* is inclined from a down side (Y(−) side) to an up side (Y(+) side) from the proximal end side (Z(−) side) toward the distal end side (Z(+) side).

Each of the side surface portions 122*b* extends along the Z direction and is configured with surfaces substantially parallel to the YZ plane. Each of the side surface portions 122*b* comprises a first side surface portion 122*f* that is positioned on a top surface portion 122*c* side and on an inclined surface portion 122*d* side, and a second side surface portion 122*g* that is positioned on an opening portion 122*a* side. A distance between the first side surface portions 122*f* facing each other is smaller than a distance between the second side surface portions 122*g* facing each other. A stepped portion 122*h* is formed between the first side surface portion 122*f* and the second side surface portion 122*g*.

The inner portion 122 comprises a flange portion 122*i* that surrounds an outer periphery of the inner portion 122. The flange portion 122*i* is provided on a proximal end side of the top surface portion 122*c* and on a proximal end side of the first side surface portion 122*f* and is also provided in the bottom surface portion 122*e* (not shown). The flange portion 122*i* is configured with four connected linear portions and is provided to surround the outer periphery of the inner portion 122.

The inclined surface portion 122*d* has a shape following the oscillator surface 51 of the ultrasound transducer 50 described above and is inclined in an arc shape from an up side (Y(+) side) to a down side (Y(−) side) from the proximal end side (Z(−) side) toward the distal end side (Z(+) side).

The side surface portions 122*b* have the two protrusion portions 122*j* facing each other on inner surfaces of the second side surface portions 122*g*. The two protrusion portions 122*j* extend to be parallel in the Y direction and protrude in a direction approaching each other.

Outer Portion

The outer portion 124 has an opening portion 124*a* at one end in the Z direction, and comprises two side surface portions 124*b* disposed to face each other, a top surface portion 124*c*, an inclined surface portion 124*d*, and a bottom surface portion 124*e*. The outer portion 124 is configured in a bottomed tubular shape having the opening portion 124*a*, and portions other than the opening portion 124*a* are closed by the two side surface portions 124*b*, the top surface portion 124*c*, the inclined surface portion 124*d*, and the bottom surface portion 124*e*.

Each side of the two side surface portions 122*b*, the top surface portion 122*c*, and the bottom surface portion 122*e* that define the opening portion 124*a* is linear, and a shape of the opening portion 124*a* is a substantially rectangular shape.

Each of the side surface portions 124*b* extends along the Z direction and is configured with surfaces substantially parallel to the YZ plane. The opening portion 124*a* of the outer portion 124 is widened to a side surface portion 124*b* side (X direction) to house the stepped portion 122*h* of the inner portion 122.

The inclined surface portion 124*d* has a shape following the oscillator surface 51 of the ultrasound transducer 50 described above and is inclined in a curved shape from the up side (Y(+) side) to the down side (Y(−) side) from the proximal end side (Z(−) side) toward the distal end side (Z(+) side).

Balloon Body

As shown in 700A, the inner portion 122 is housed in the outer portion 124 through the opening portion 124*a* of the outer portion 124, and the outer portion 124 covers the inner portion 122. Note that the outer portion 124 does not need to cover the entire inner portion 122. The outer portion 124 covers the two first side surface portions 122*f*, the top surface portion 122*c*, the inclined surface portion 122*d*, and a part (distal end side) of the bottom surface portion 122*e* of the inner portion 122. On the other hand, the outer portion 124 does not cover the second side surface portions 122*g* and a part (proximal end side) of the bottom surface portion 122*e* of the inner portion 122.

As shown in 700A, the two side surface portions 122*b* and the two side surface portions 124*b* that configure the inner portion 122 and the outer portion 124 are disposed to face each other, respectively, the top surface portion 122*c* and the top surface portion 124*c* are disposed to face each other, the inclined surface portion 122*d* and the inclined surface portion 124*d* are disposed to face each other, and the bottom surface portion 122*e* and the bottom surface portion 124*e* are disposed to face each other.

A peripheral edge portion of the opening portion 124*a* of the outer portion 124 comes into contact with the flange portion 122*i* of the inner portion 122. With the flange portion 122*i*, a relative position of the outer portion 124 with respect to the inner portion 122 is determined.

The outer portion 124 is bonded on the opening portion 122*a* side of the inner portion 122, and the balloon body 121 having the two-layer structure is configured. The balloon body 121 is configured in a bottomed tubular shape that has the opening portion 122*a* provided at one end in the Z direction of the insertion portion 12 and attached to the distal end part body 34.

As a material for the balloon body 121, to make a configuration in which it is difficult for the inner portion 122 and the outer portion 124 to adhere to each other, it is preferable that the inner portion 122 and the outer portion 124 are formed of different materials. Note that, as described below, a clearance is provided between the inner portion 122 and the outer portion 124, whereby it is possible to prevent the inner portion 122 and the outer portion 124 from adhering to each other. Accordingly, the inner portion 122 and the outer portion 124 may be formed of the same material. As the materials for the inner portion 122 and the outer portion 124, silicon rubber, natural rubber, or the like can be used.

In a case where the balloon 120 is mounted on the distal end part body 34, the first side surface portions 122*f* of the inner portion 122 and the standing wall portions 91 are disposed to face each other, and the inclined surface portion 122*d* and the ultrasound transducer 50 are disposed to face each other. The side surface portions 124*b* of the outer portion 124 and the standing wall portions 91 are disposed to face each other with the first side surface portions 122*f* interposed therebetween, and the inclined surface portion 124*d* and the ultrasound transducer 50 are disposed to face each other with the inclined surface portion 122*d* interposed therebetween.

The opening portion 122*a* provided in the inner portion 122 is an insertion port into which the distal end part body 34 is inserted. An internal space of the inner portion 122 is a similar shape to the shape of the distal end part body 34, and is formed in a shape smaller than an outer shape of the distal end part body 34. A width (a length in the X direction) of the two side surface portions 122*b* of the balloon 120 before being mounted on the distal end part body 34 is smaller than a distance between the two standing wall portions 91 in the width direction. As a result, in a case of being inserted into the distal end part body 34 from the opening portion 122*a* of the inner portion 122, the two side surface portions 122*b* of the inner portion 122 expand in the X direction, and due to contractile force of the inner portion 122 to return, the side surface portions 122*b* are in close contact with and fixed to the standing wall portions 91. The two side surface portions 122*b* of the inner portion 122 function as a fixing portion that is in close contact with and fixed to the distal end part body 34.

The two protrusion portions 122*j* provided in the second side surface portions 122*g* that configure the side surface portions 122*b* of the inner portion 122 are fitted into the groove portions 92 of the distal end part body 34 in a case where the balloon 120 is mounted on the distal end part body 34. The two protrusion portions 122*j* that are fitted into the groove portions 92 of the distal end part body 34 are provided in the side surface portions 122*b* that function as the fixing portion. In a case where the groove portions 92 are provided in the standing wall portions 91, the two protrusion portions 122*j* are provided in the first side surface portions 122*f* that configure the side surface portion 122*b*.

The inside of the inner portion 122 is formed in a similar shape to the distal end part body 34 and in a shape smaller than the outer shape of the distal end part body 34, whereby the inner portion 122 can be in close contact and fixed from the oscillator surface 51 and the surface on the opposite side to the oscillator surface 51. As a result, the inner portion 122 can also be in close contact with and fixed to the oscillator surface 51 and to the surface on the opposite side to the oscillator surface 51 of the distal end part body 34, and the balloon 120 can be firmly fixed to the distal end part body 34. The inclined surface portion 122*d* and the bottom surface portion 122*e* of the inner portion 122 function as a fixing portion that is in close contact with and fixed to the distal end part body 34.

It is preferable that the balloon body 121 has a shape following an outer shape of the oscillator surface of the ultrasound transducer 50. With the balloon body 121 having such a configuration, it is possible to stabilize an orientation in a case where the balloon 120 is mounted on the distal end part body 34.

Figure 8:
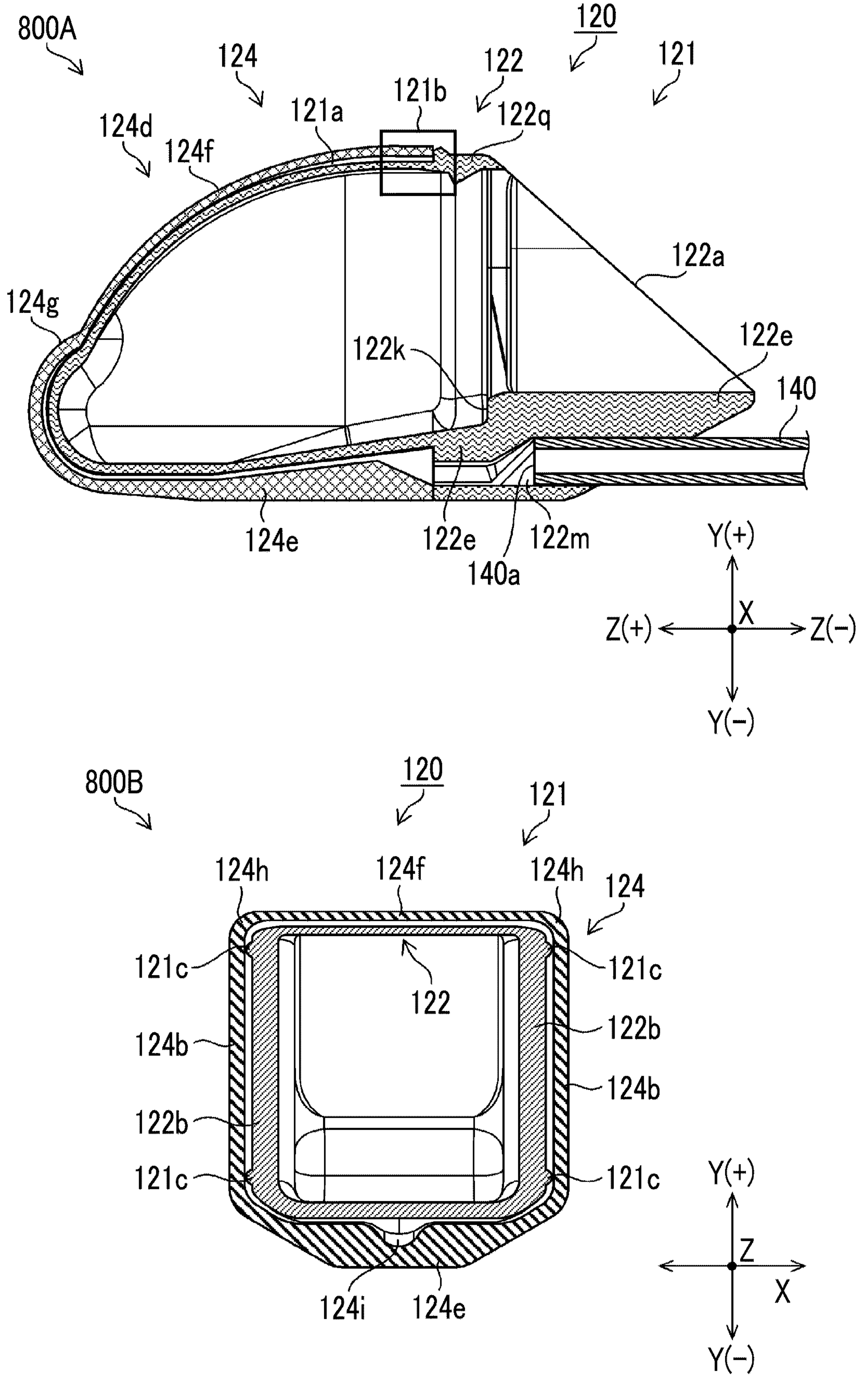
FIG. 8 is a sectional view of the balloon for an ultrasonic endoscope.

FIG. 8 is a sectional view of the balloon 120. 800A is a sectional view of the balloon 120 taken along the YZ plane, and 800B is a sectional view of the balloon 120 taken along the XY plane. As shown in FIG. 8, the outer portion 124 covers the inner portion 122, and the outer portion 124 and the inner portion 122 are bonded, whereby the balloon body 121 is configured.

As shown in 800A, the inner portion 122 and the outer portion 124 are bonded, and a closed space can be formed between the inner portion 122 and the outer portion 124. This space is a storage portion 121*a* that stores an ultrasonic wave transmission medium. Since the ultrasonic wave transmission medium is stored in the storage portion 121*a*, an oscillator surface region 124*f* that configures the inclined surface portion 124*d* of the outer portion 124 can be swollen. The oscillator surface region 124*f* functions as a swelling portion. The oscillator surface region 124*f* is a region facing the oscillator surface 51 of the ultrasound transducer 50.

As described above, since the storage portion 121*a* of the balloon 120 is configured with the closed space between the inner portion 122 and the outer portion 124, it is possible to secure fluid-tightness in the balloon 120 itself. Accordingly, unlike the related art in which fluid-tightness is secured between the distal end part body and the balloon, it is not required that the balloon 120 has an annular groove shape in locking the distal end part body and the balloon. With the balloon 120, it is possible to avoid an increase in diameter and an increase in size of the distal end part body 34 due to the annular groove shape. The balloon 120 gives a degree of freedom for design to the shape of the distal end part body 34. As shown in FIG. 7, the opening portion 122*a* of the balloon 120 can have a rectangular shape, instead of an annular shape.

It is preferable that the inner portion 122 and the outer portion 124 are not in close contact, and that a clearance is provided therebetween. Since the inner portion 122 and the outer portion 124 are not in close contact, it is possible to prevent supplying the ultrasonic wave transmission medium from becoming difficult in a case of supplying the ultrasonic wave transmission medium to the storage portion 121*a* since an outer surface of the inner portion 122 and an inner surface of the outer portion 124 adhere to each other. As described below, in a case of adhering and assembling the inner portion 122 and the outer portion 124, it can be made difficult for the inner portion 122 and the outer portion 124 to adhere to each other. The clearance means a state in which the outer surface of the inner portion 122 and the inner surface of the outer portion 124 are separated from each other by a given distance.

As shown in 800A, in a region surrounded by a quadrangle, the inner portion 122 and the outer portion 124 are bonded by an adhesive or the like. A clearance is not present in an adhesion portion 121*b* of the inner portion 122 and of the outer portion 124 bonded by the adhesive. The clearance may not be provided in the entire region between the inner portion 122 and the outer portion 124.

The adhesion portion 121*b* may be, for example, at a position corresponding to the top surface portion 122*c* (not shown) of the inner portion 122 and to the top surface portion 124*c* (not shown) of the outer portion 124.

The adhesion portion 121*b* does not expand even though the ultrasonic wave transmission medium is supplied into the balloon 120. Thus, even though the puncture needle 100 is led out from the outlet port 52, the proximal end side (Z(−) side) of the balloon 120 does not expand. Therefore, it is possible to prevent the puncture needle 100 led out from the outlet port 52 from being brought into contact with the swollen balloon 120. The adhesion portion 121*b* functions as a swelling restricting portion capable of suppressing swelling except in the oscillator surface region 124*f* described below. The adhesion portion 121*b* suppresses swelling of a proximal end side (Z(−) side) of the oscillator surface region 124*f*.

The inclined surface portion 124*d* of the outer portion 124 includes the oscillator surface region 124*f* and a thick portion 124*g*. The thick portion 124*g* is disposed on the other end side (Z(+) side) opposite to one end side (Z(−) side) in the Z direction and is formed to have a thickness greater than a thickness of the oscillator surface region 124*f*. The thick portion 124*g* suppresses swelling of a distal end side (Z(+) side) of the oscillator surface region 124*f* of the outer portion 124 in a case where the ultrasonic wave transmission medium is supplied to the storage portion 121*a*. The thick portion 124*g* functions as a swelling restricting portion and can make the oscillator surface region 124*f* more effectively swollen.

Since the oscillator surface region 124*f* is formed to have a film thickness thinner than other regions of the outer portion 124 including the thick portion 124*g*, the oscillator surface region 124*f* can be easily swollen compared to other regions.

The bottom surface portion 122*e* of the inner portion 122 that functions as a fixing portion of the balloon 120 has the locking portion 122*k* inside. The locking portion 122*k* is configured with a plane substantially parallel to the XY plane and stands in the Y(+) direction as viewed from the distal end side (Z(+) side). The locking portion 122*k* is locked to the stepped portion 94 of the distal end part body 34 in a case where the balloon 120 is mounted on the distal end part body 34.

The inner portion 122 of the balloon body 121 has a communication path 122*m* that communicates with the storage portion 121*a*, in the bottom surface portion 122*e* on an opposite side to the oscillator surface region 124*f*. The communication path 122*m* has an opening in the Z(−) direction, and the storage portion 121*a* communicates with the outside through the communication path 122*m*.

A tube 140 is inserted into the communication path 122*m* of the bottom surface portion 122*e* of the inner portion 122 that functions as a fixing portion of the balloon 120, whereby it is possible to attach the tube 140 to the balloon 120. The attachment of the tube 140 to the balloon 120 may be attachable and detachable or may be inseparable. The tube 140 is a tubular member that has a space to be a flow channel inside. The ultrasonic wave transmission medium can be supplied from the flow channel of the tube 140 to the storage portion 121*a* in the balloon 120 through the communication path 122*m*. As a result, it is possible to expand the oscillator surface region 124*f* that configures the outer portion 124 of the balloon 120. Since the tube 140 is attached to the balloon 120, a supply pipe line for supplying the ultrasonic wave transmission medium to the balloon 120 does not need to be provided in the insertion portion 12 of the endoscope 1. Thus, it is possible to achieve a reduction in diameter of the insertion portion 12. The balloon 120 (and the tube 140) is disposable, whereby there is no need to perform cleaning and sterilization of the tube 140. In recent years, a minimum pipe line diameter to be sterilized by a sterilization device has been defined, and there has been an increasing demand for cleaning, disinfection, and sterilization. By making the tube 140 disposable, it is possible to omit the work of cleaning and sterilization of a supply pipe line.

The tube 140 is configured to expand less easily than the balloon body 121 (inner portion 122 and outer portion 124). That is, the balloon body 121 is configured to expand more easily than the tube 140. A configuration in which the balloon body 121 expands more easily than the tube 140 can be realized, for example, by making a film thickness of the balloon body 121 thinner than a film thickness of the tube 140 or by using a material having an expansion coefficient greater than the material for the tube 140, as the material for the balloon body 121.

As shown in 800B, the outer portion 124 has the side surface portions 124*b* (that is, thick portions) that are formed to have a thickness greater than the thickness of the oscillator surface region 124*f*, on both sides in the X direction perpendicular to the Z direction of the oscillator surface region 124*f*. The outer portion 124 has transition portions 124*h* that connect the oscillator surface region 124*f* and the side surface portions 122*b*. The transition portions 124*h* increase in thickness from the oscillator surface region 124*f* toward the side surface portions 124*b*. The transition portions 124*h* can suppress swelling of the oscillator surface region 124*f* in the X direction in a case where the ultrasonic wave transmission medium is supplied to the storage portion 121*a*, and function as a swelling restricting portion. The transition portions 124*h* can be configured with a part on the Y(+) side of the side surface portions 124*b*.

In the balloon body 121, the side surface portions 122*b* of the inner portion 122 and the side surface portions 124*b* of the outer portion 124 are disposed to face each other on both sides in the X direction perpendicular to the Z(+) direction of the oscillator surface region 124*f*. The balloon body 121 has adhesion regions 121*c* where the inner portion 122 and the outer portion 124 are adhered by an adhesive or the like, between the side surface portions 122*b* and the side surface portion 124*b* facing each other. The adhesion regions 121*c* suppress swelling of the oscillator surface region 124*f* in the X direction in a case where the ultrasonic wave transmission medium is supplied to the storage portion 121*a*, and function as a swelling restricting portion. The adhesion regions 121*c* may be partial regions between the side surface portions 122*b* and the side surface portion 124*b* as shown in 800B or may be the entire regions between the side surface portions 122*b* and the side surface portion 124*b* facing each other.

The bottom surface portion 124*e* of the outer portion 124 has a recess portion 124*i* that has a semispherical shape in a sectional view and that extends in the Z direction, at substantially a center in the width direction (X direction). The recess portion 124*i* is a portion that configures a part of the clearance and that communicates with the communication path 122*m* of the inner portion 122. It is possible to easily supply the ultrasonic wave transmission medium to the storage portion 121*a* with the recess portion 124*i*.

Figure 9:
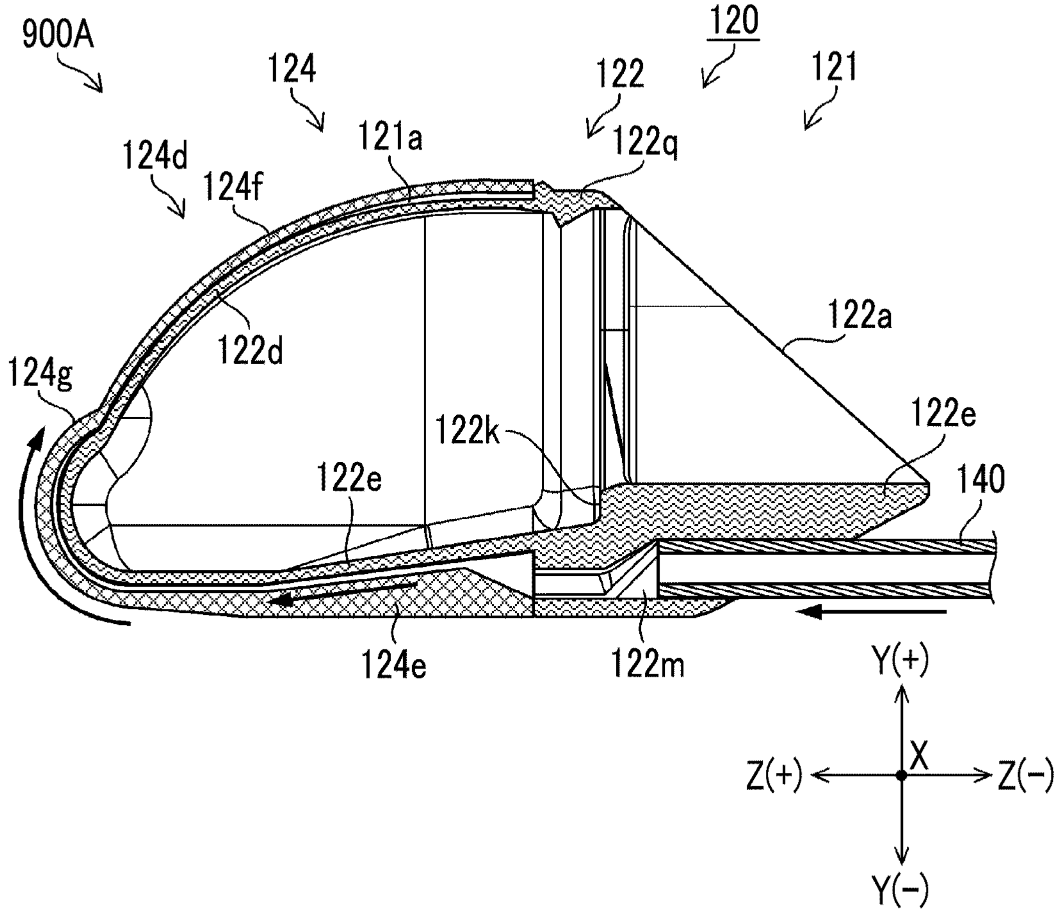
FIG. 9 is a sectional view illustrating a flow of an ultrasonic wave transmission medium that is supplied to the balloon for an ultrasonic endoscope.
Figure 9:
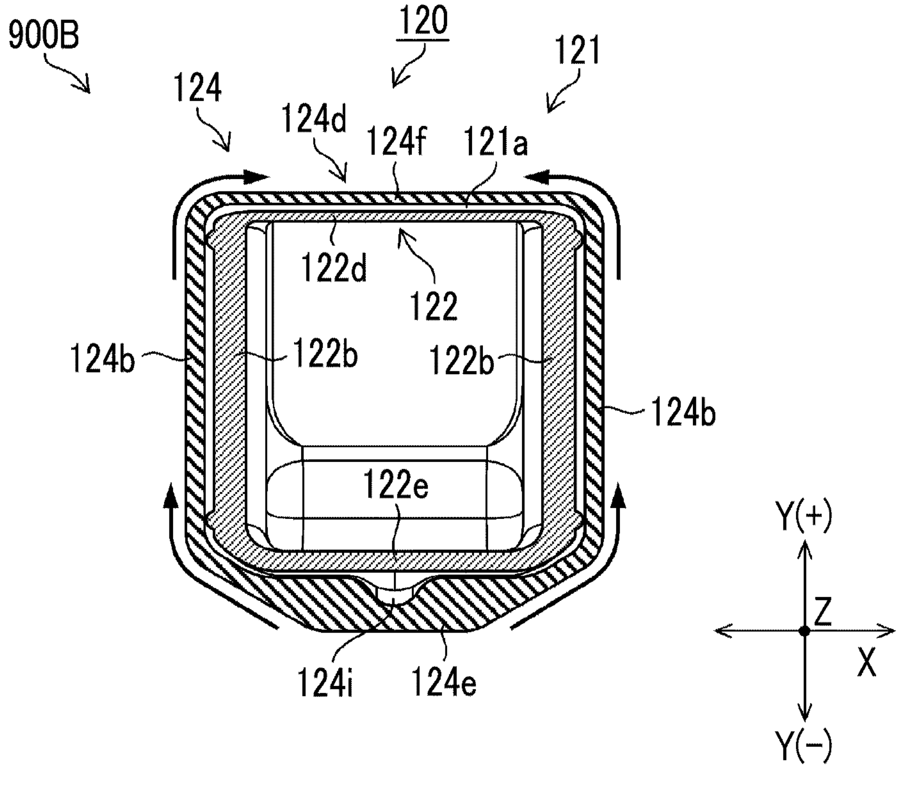

FIG. 9 is a sectional view of the balloon 120 illustrating a flow of the ultrasonic wave transmission medium supplied to the balloon 120. 900A is a sectional view of the balloon 120 taken along the YZ plane, and 900B is a sectional view of the balloon 120 taken along the XY plane.

A flow channel through which the ultrasonic wave transmission medium is supplied to the storage portion 121*a* will be described with reference to FIG. 9. As shown in 900A, the tube 140 is attached to the communication path 122*m* of the outer portion 124 for supplying the ultrasonic wave transmission medium to the storage portion 121*a*. Since the tube 140 is disposed on an opposite side (Y(−) side) to the oscillator surface region 124*f*, swelling of the oscillator surface region 124*f* is not inhibited. In addition, the acquisition of the observation image with the observation optical system 40 is not inhibited.

The ultrasonic wave transmission medium is supplied to the balloon 120 through the tube 140. The ultrasonic wave transmission medium is supplied to a region having the clearance between the inner portion 122 and the outer portion 124 through the communication path 122*m* of the inner portion 122. A region between the bottom surface portion 122*e* of the inner portion 122 and the bottom surface portion 124*e* of the outer portion 124 is filled with the ultrasonic wave transmission medium, and a region between the inclined surface portion 122*d* of the inner portion 122 and the inclined surface portion 124*d* of the outer portion 124 is filled with the ultrasonic wave transmission medium. The ultrasonic wave transmission medium is finally stored in the storage portion 121*a* that is mainly configured with the oscillator surface region 124*f* and the inclined surface portion 122*d*.

As shown in 900B, a region between the bottom surface portion 122*e* of the inner portion 122 and the bottom surface portion 124*e* of the outer portion 124 is filled with the ultrasonic wave transmission medium, and a region between the side surface portion 122*b* of the inner portion 122 and the side surface portion 124*b* of the outer portion 124 is filled with the ultrasonic wave transmission medium. The ultrasonic wave transmission medium is finally stored in the storage portion 121*a* that is mainly configured with the oscillator surface region 124*f* and the inclined surface portion 122*d*.

Figure 10:
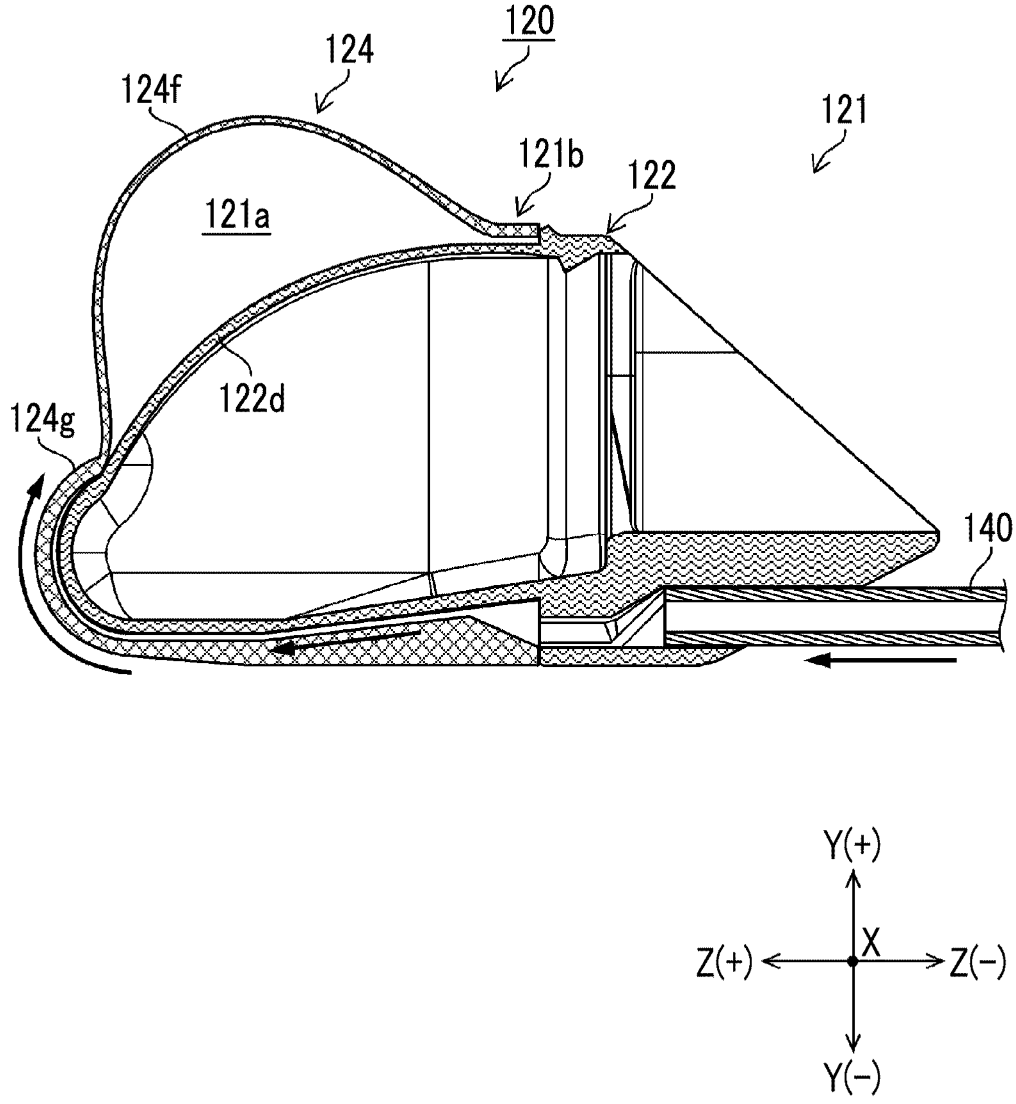
FIG. 10 is a sectional view showing a state in which an oscillator surface region of the balloon for an ultrasonic endoscope is swollen.

FIG. 10 is a sectional view showing a state in which the oscillator surface region 120*f* of the balloon 120 is swollen, and is a sectional view of the balloon 120 taken along the YZ plane. As shown in FIG. 10, in a case where the ultrasonic wave transmission medium is stored in the storage portion 121*a*, the oscillator surface region 124*f* is most swollen.

The oscillator surface region 124*f* has a film thickness thinner than other regions of the outer portion 124 including the thick portion 124*g*. As a result, the oscillator surface region 124*f* is more easily swollen than other regions.

In regions other than the oscillator surface region 124*f*, for example, the thick portion 124*g*, the adhesion portion 121*b*, the transition portions 124*h* (not shown), and the adhesion regions 121*c* (not shown) that function as a swelling restricting portion are provided. With the thick portion 124*g* and the adhesion portion 121*b*, swelling of regions (regions in the Z(+) direction and the Z(−) direction with respect to the oscillator surface region 124*f*) other than the oscillator surface region 124*f* is suppressed. With the transition portions 124*h* and the adhesion regions 121*c*, swelling of regions (regions in the X direction with respect to the oscillator surface region 124*f*) other than the oscillator surface region 124*f* is suppressed.

In the balloon 120, the oscillator surface region 124*f* is made most swollen, whereby it is possible to suppress swelling of a bottom surface side and side surface sides of the balloon 120, and to insert the distal end part body 34 to a periphery in a case of inserting the distal end part body 34 with the balloon 120 mounted thereon into the body cavity.

The tube 140 is a member that does not expand compared to the balloon 120. Accordingly, in a case where the ultrasonic wave transmission medium is supplied to the balloon 120 through the tube 140, since expansion of the tube 140 is suppressed, it is possible to effectively supply the ultrasonic wave transmission medium to the balloon 120.

Figure 11:
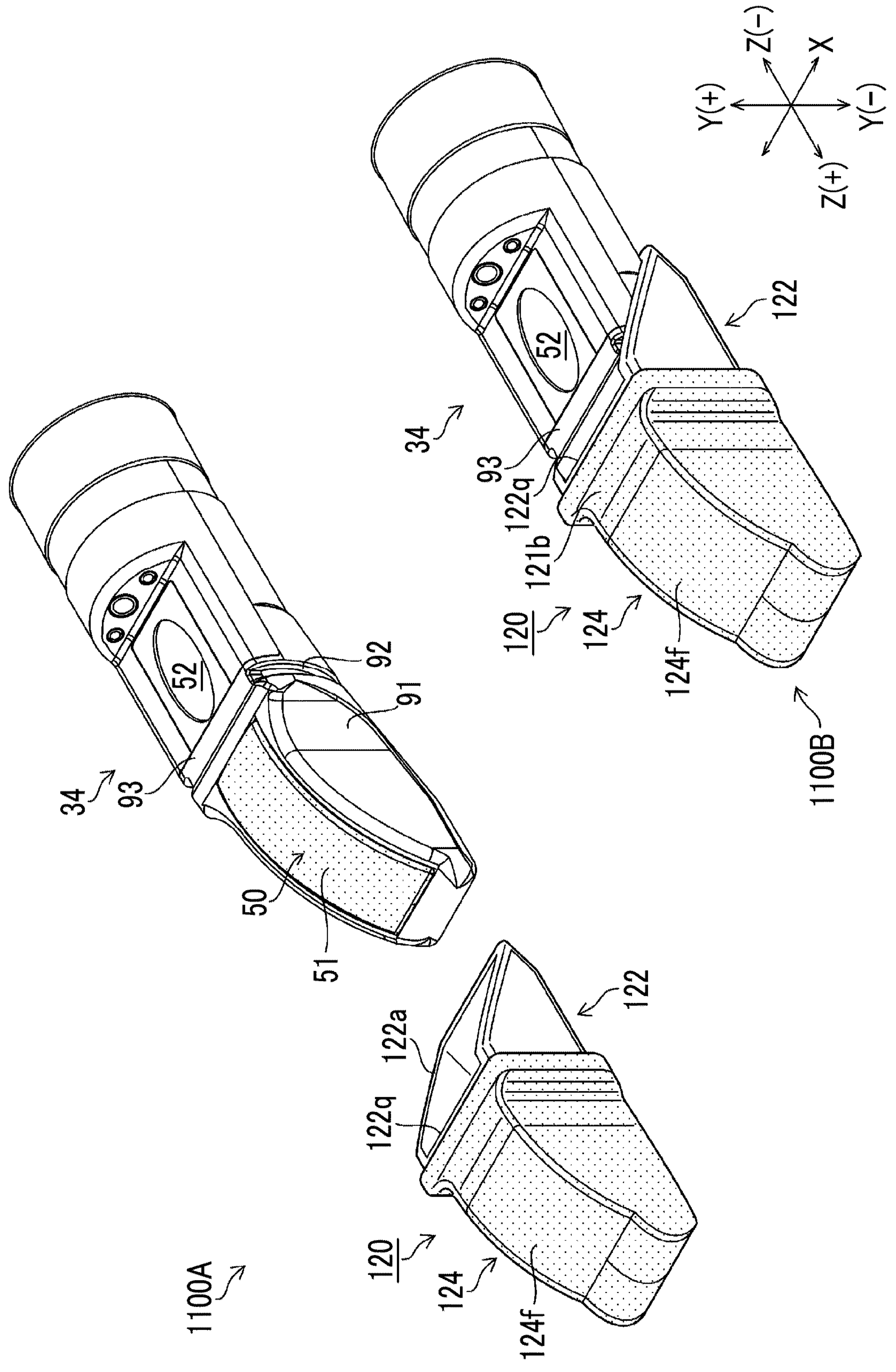
FIG. 11 is a perspective view illustrating mounting of the balloon for an ultrasonic endoscope, with the tube omitted, on the distal end part body.

Next, mounting of the balloon 120 on the distal end part body 34 will be described. FIG. 11 is a perspective view illustrating mounting of the balloon 120, with the tube 140 omitted, on the distal end part body 34. 1100A shows a state before the balloon 120 is mounted on the distal end part body 34. The opening portion 122*a* of the balloon 120 and the distal end side of the distal end part body 34 are aligned. 1100B shows a state after the balloon 120 is mounted on the distal end part body 34. The opening portion 122*a* of the balloon 120 is attached to the distal end part body 34, and the balloon 120 is mounted on the distal end part body 34. The inner portion 122 covers the ultrasound transducer 50 of the ultrasonic attachment portion 34*a* and further covers a part of an outer peripheral surface of the outlet port forming portion 34*b* other than the opening forming surface 71. The outer portion 124 is disposed at a position covering the ultrasound transducer 50 of the ultrasonic attachment portion 34*a*.

As described above, at least the side surface portions 122*b* are in close contact with and fixed to the standing wall portions 91 by contractile force of the side surface portion 122*b* (not shown) as a fixing portion of the inner portion 122.

A flat portion 122*q* of the inner portion 122 that functions as a fixing portion is provided on the proximal end side of the oscillator surface region 124*f* of the balloon 120 that functions as a swelling portion. The plane portion 93 between the ultrasound transducer 50 and the outlet port 52 is in close contact with and fixed to the flat portion 122*q* of the balloon 120. Since the flat portion 122*q* is provided, it is possible to extend a distance between the oscillator surface region 124*f* and the outlet port 52. Therefore, it is possible to prevent the puncture needle 100 led out from the outlet port 52 from being brought into contact with the swollen balloon 120. The flat portion 122*q* may be at a position of the adhesion portion 121*b* described above.

Since the balloon 120 has a shape in which the ultrasound transducer 50 is offset, as a whole, it is possible to allow a worker to easily recognize an orientation in which the balloon 120 is mounted on the distal end part body 34.

With the balloon 120 of the present embodiment, the inner portion 122 and the outer portion 124 are bonded to form a sealed space, and the sealed space is used as the storage portion 121*a* that stores the ultrasonic wave transmission medium. Accordingly, the outer shape of the distal end part body 34 is not limited to a shape for securing fluid-tightness and can be designed in consideration of a reduction in diameter of the distal end part body 34 and a lead-out route of the puncture needle 100.

In a case where the tube 140 is attached to the balloon 120 and the ultrasonic wave transmission medium is supplied to the storage portion 121*a* through the tube 140, as shown in FIG. 11, there is no need to provide a supply pipe line in the distal end part body 34 of the endoscope 1.

Figure 12:
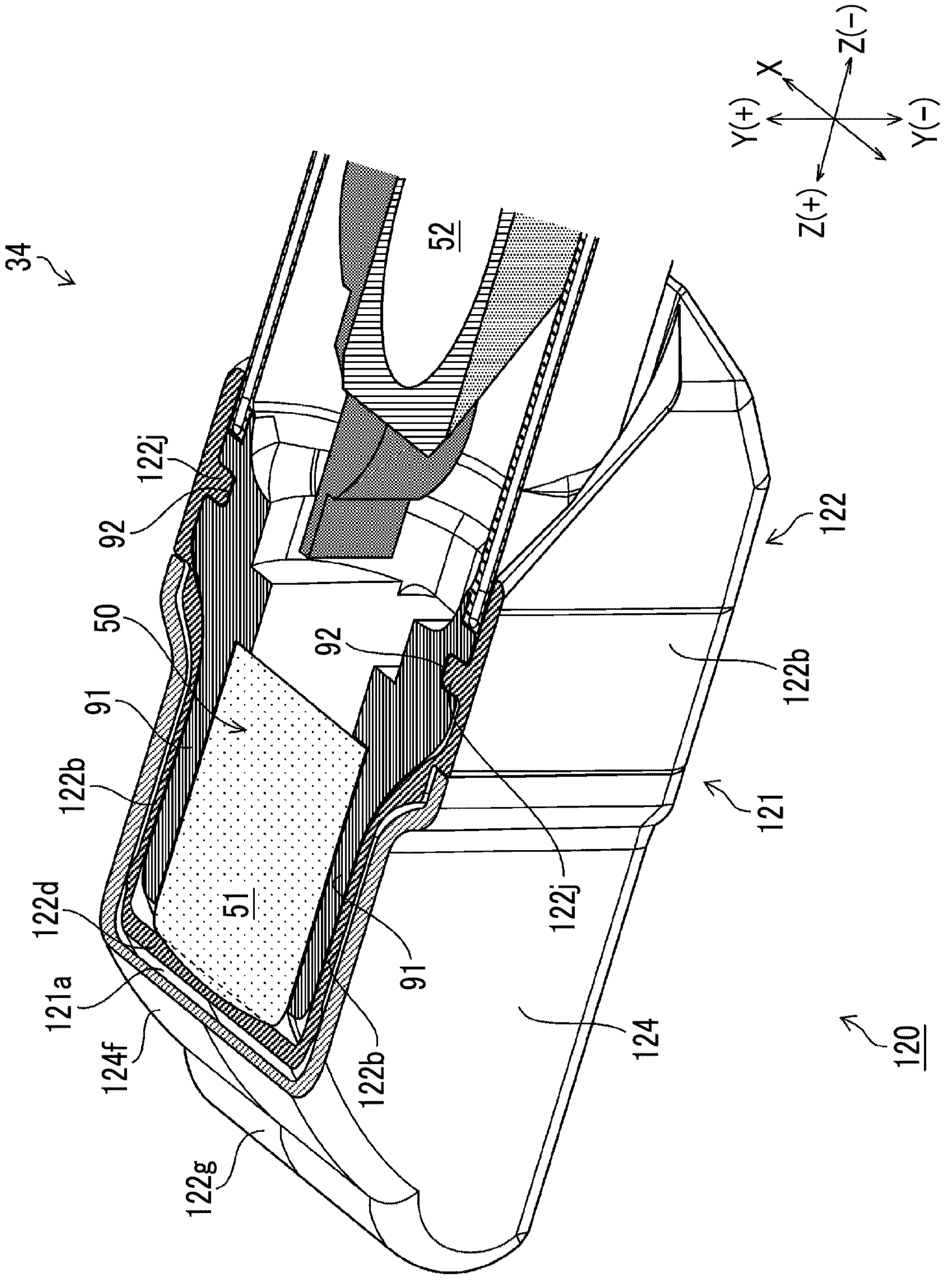
FIG. 12 is a perspective view of a distal end part body on which the balloon for an ultrasonic endoscope, with the tube omitted, is mounted, taken along an XZ plane.

FIG. 12 is a diagram of the distal end part body 34 on which the balloon 120, with the tube 140 omitted, is mounted, taken along the XZ plane. As shown in FIG. 12, the side surface portion 122*b* as a fixing portion of the inner portion 122 that configures the balloon 120 has the protrusion portions 122*j*. The groove portions 92 are provided between the ultrasound transducer 50 and the outlet port 52. The protrusion portions 122*j* and the groove portions 92 are fitted. Since the groove portions 92 and the protrusion portions 122*j* are fitted, movement in a direction in which the balloon 120 and the distal end part body 34 are separated from each other is restricted, and it can be made difficult for the balloon 120 to fall off from the distal end part body 34.

In a case where the standing wall portions 91 have groove portions (not shown), protrusion portions (not shown) are provided in the side surface portions 122*b* of the balloon 120 facing the ultrasound transducer 50. The protrusion portions and the groove portions are fitted, whereby it can be made difficult for the balloon 120 to fall off from the distal end part body 34.

The balloon 120 has the storage portion 121*a* between the oscillator surface region 124*f* facing the oscillator surface 51 and the inclined surface portion 122*d*.

Figure 13:
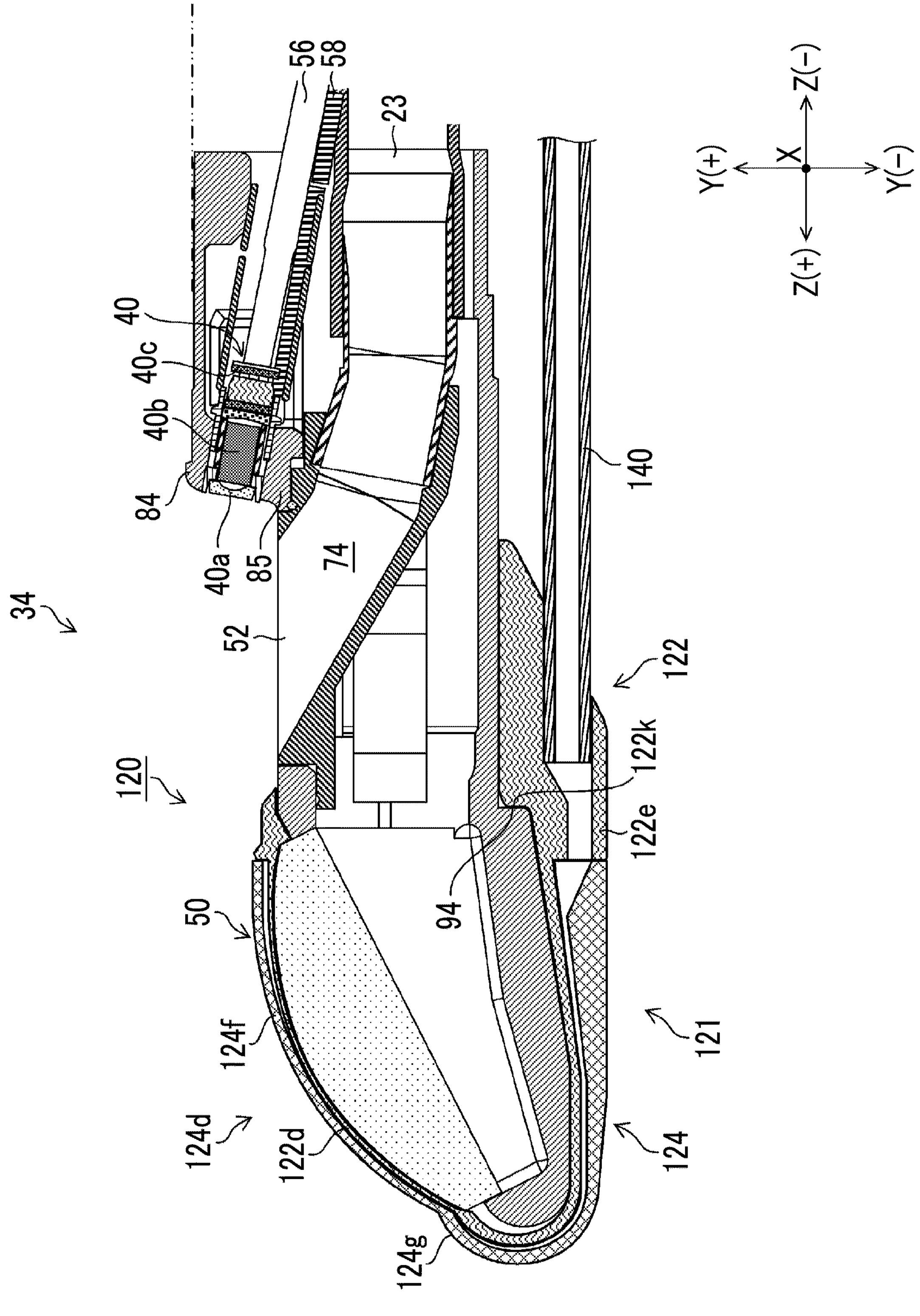
FIG. 13 is a sectional view of the distal end part body on which the balloon for an ultrasonic endoscope is mounted, taken along a YZ plane.

FIG. 13 shows a cross section of the distal end part body 34 on which the balloon 120 is mounted, taken along the YZ plane. As shown in FIG. 13, the distal end part body 34 has the stepped portion 94 in a surface on the opposite side to the oscillator surface 51 on the proximal end side (Z(−) direction side) of the ultrasound transducer 50. The bottom surface portion 122*e* as a fixing portion of the inner portion 122 that configures the balloon 120 has the locking portion 122*k*. The stepped portion 94 and the locking portion 122*k* are locked, whereby it is possible to prevent the balloon 120 from falling off from the distal end part body 34. It is possible to prevent the balloon 120 from falling off in a case where the insertion portion 12 of the endoscope 1 on which the balloon 120 is mounted is pulled out from the body cavity in the Z(−) direction. The tube 140 is attached to be parallel with the insertion portion 12 and is connected to a supply/discharge unit of the ultrasonic wave transmission medium, such as a syringe, near the operating portion 10.

Figure 14:
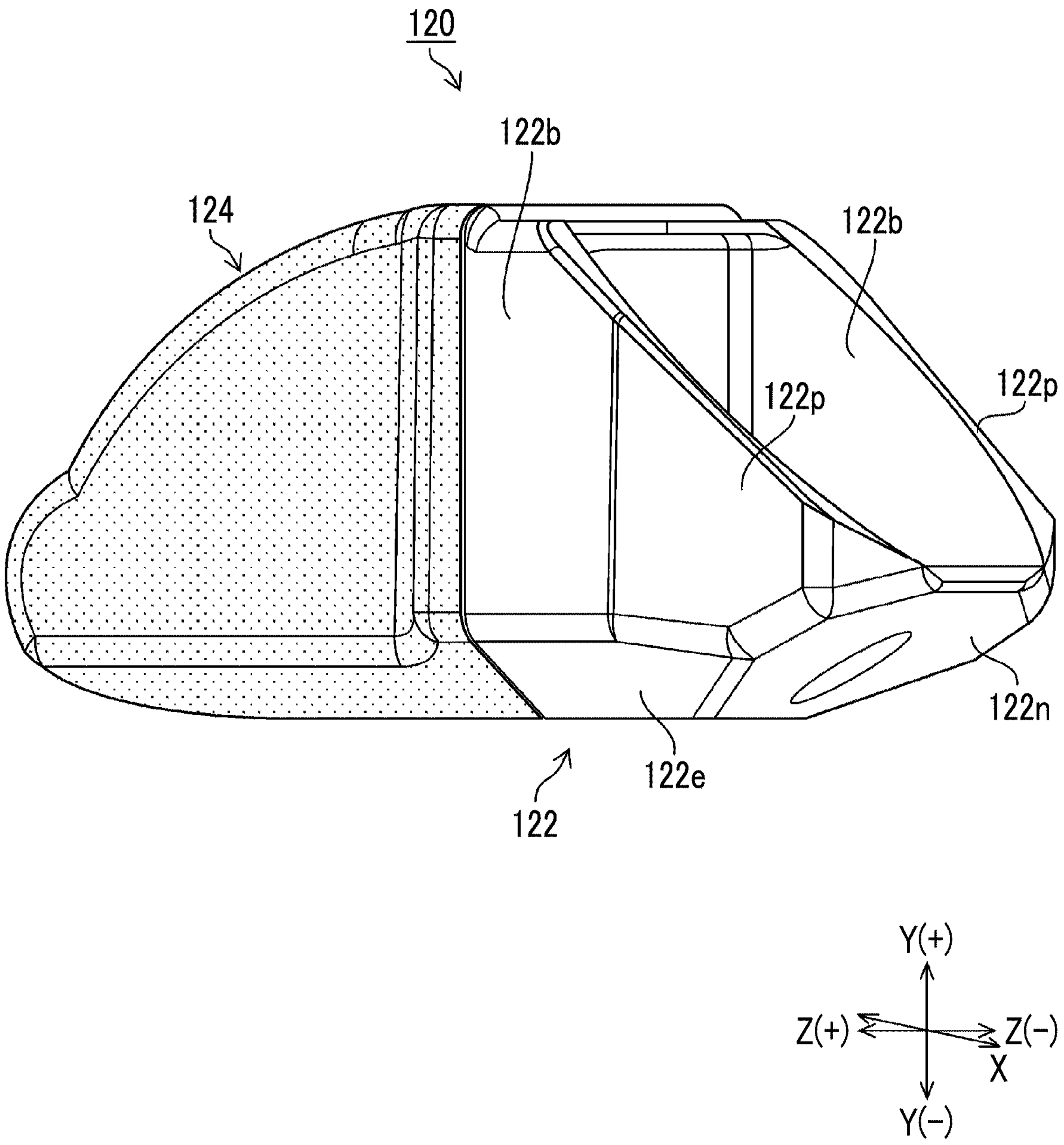
FIG. 14 is a perspective view as the balloon for an ultrasonic endoscope with the tube omitted is viewed from a proximal end side.

FIG. 14 is a perspective view of the balloon 120, with the tube 140 omitted, as viewed from the Z(−) direction to the Z(+) direction. The bottom surface portion 122*e* of the inner portion 122 has a tapered portion 122*n* on the proximal end side (Z(−) side). The tapered portion 122*n* is inclined in the Y(+) direction while extending in the Z(−) direction. The two side surface portions 122*b* of the inner portion 122 have tapered portions 122*p* on the proximal end side (Z(−) side), respectively. The two tapered portions 122*p* are inclined in an orientation approaching each other while extending in the Z(−) direction.

Since the tapered portions 122*n* are provided, force in the first direction (Z direction) can be released in the Y direction. Since the tapered portion 122*p* is provided, force in the first direction (Z direction) can be released in the X direction. As a result, in a case where the distal end part is inserted into and pulled out from the body cavity, force applied due to contact with a tissue in the body can be released in the Y direction and in the X direction. Therefore, it is possible to prevent the balloon 120 from falling off from the distal end part body 34.

Although a case where the balloon 120 has the tapered portions 122*n* and the tapered portion 122*p* has been described, any one of the tapered portions 122*n* or the tapered portion 122*p* may be provided.

Ultrasonic Wave Transmission Medium Supply/Discharge Member

Figure 15:
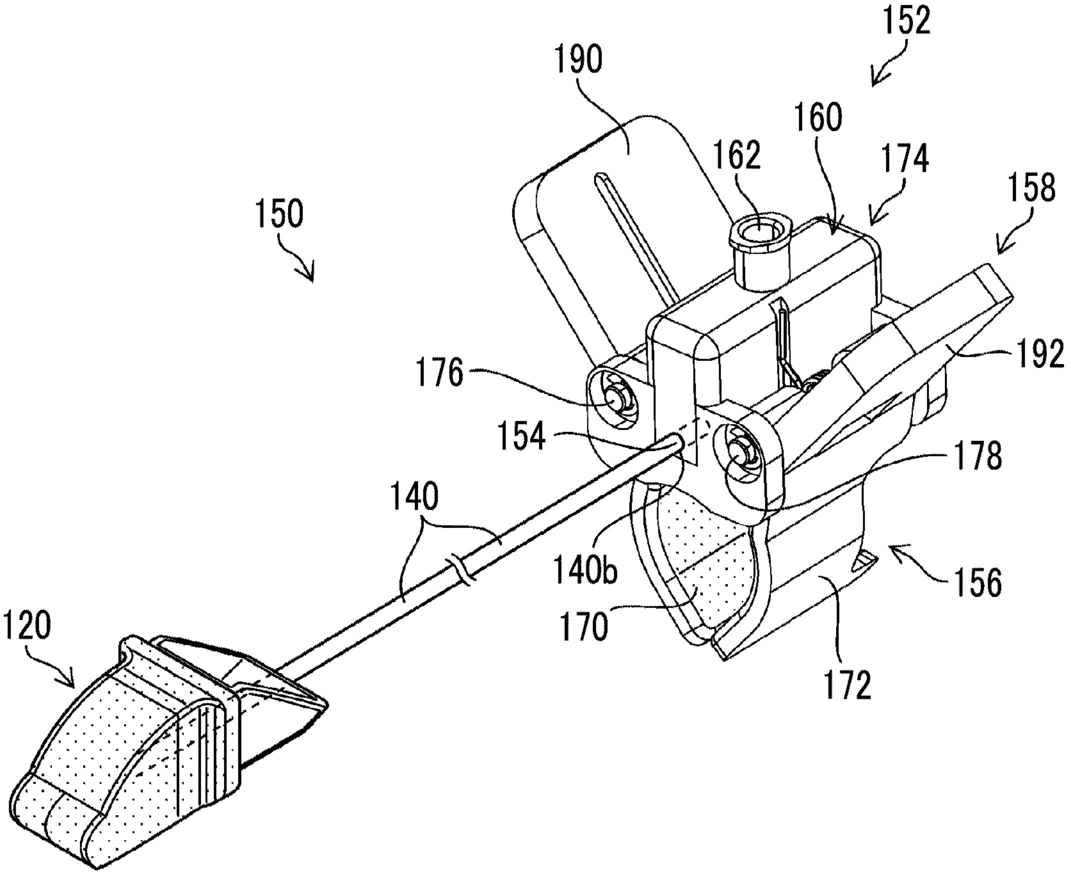
FIG. 15 is an overall perspective view of an ultrasonic wave transmission medium supply/discharge member of an embodiment.

Next, an ultrasonic wave transmission medium supply/discharge member of the embodiment will be described. FIG. 15 is an overall perspective view of the ultrasonic wave transmission medium supply/discharge member 150 of the embodiment.

As shown in FIG. 15, the ultrasonic wave transmission medium supply/discharge member 150 of the embodiment is an example of an ultrasonic wave transmission medium supply/discharge member of the embodiment of the present invention, and comprises the balloon 120, the tube 140, and a fixing portion 152. The balloon 120 is mounted to cover an outer surface of the ultrasound transducer 50 described above, and is an example of a balloon for an ultrasonic endoscope of the embodiment of the present invention. The tube 140 is in communication with the inside of the storage portion 121*a* of the balloon 120, and is an example of the tube of the embodiment of the present invention. The tube 140 is connected to the balloon 120 by attaching a distal end opening portion 140*a* (see FIG. 8) of the tube 140 to the communication path 122*m* of the balloon 120.

The fixing portion 152 can be attachably and detachably fixed to the operating portion 10 of the endoscope 1 as described below, and is connected to the balloon 120 through the tube 140. The tube 140 is connected to the fixing portion 152 by mounting a proximal end opening portion 140*b* of the tube 140 on a hole portion 154 of the fixing portion 152 to be described below. The fixing portion 152 is an example of the fixing portion according to the embodiment of the present invention.

Figure 16:
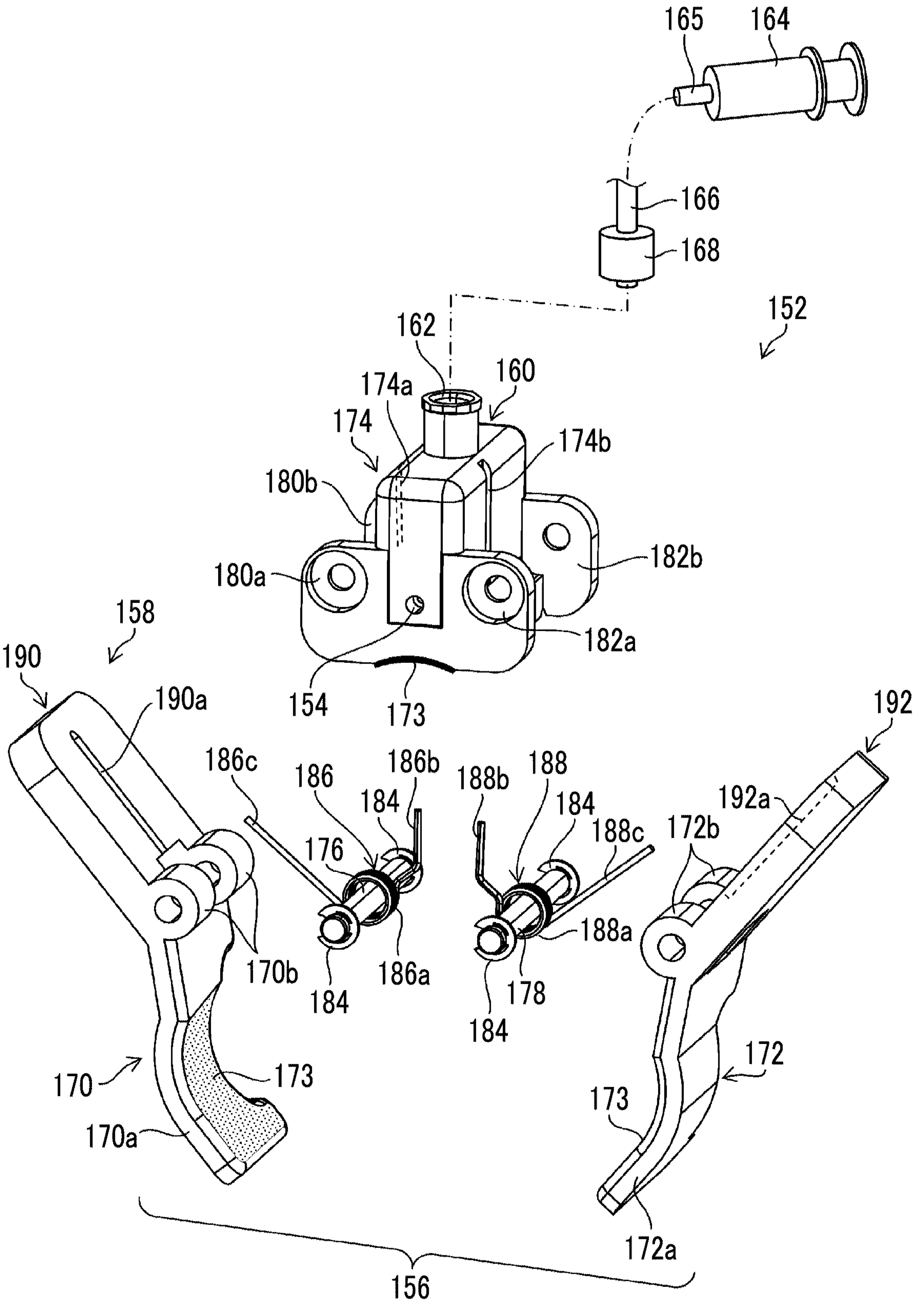
FIG. 16 is an assembly perspective view showing a configuration of a fixing portion.
Figure 17:
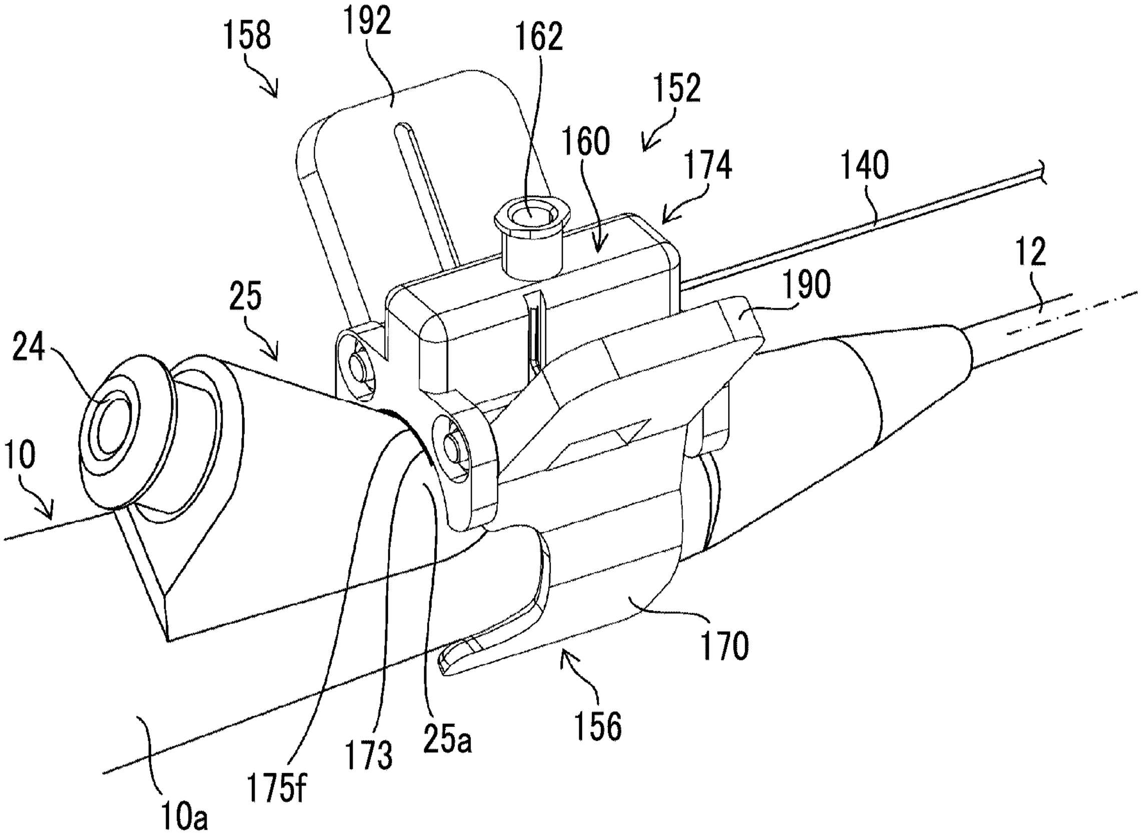
FIG. 17 is a perspective view of a fixing portion viewed from a proximal end side of an operating portion.
Figure 18:
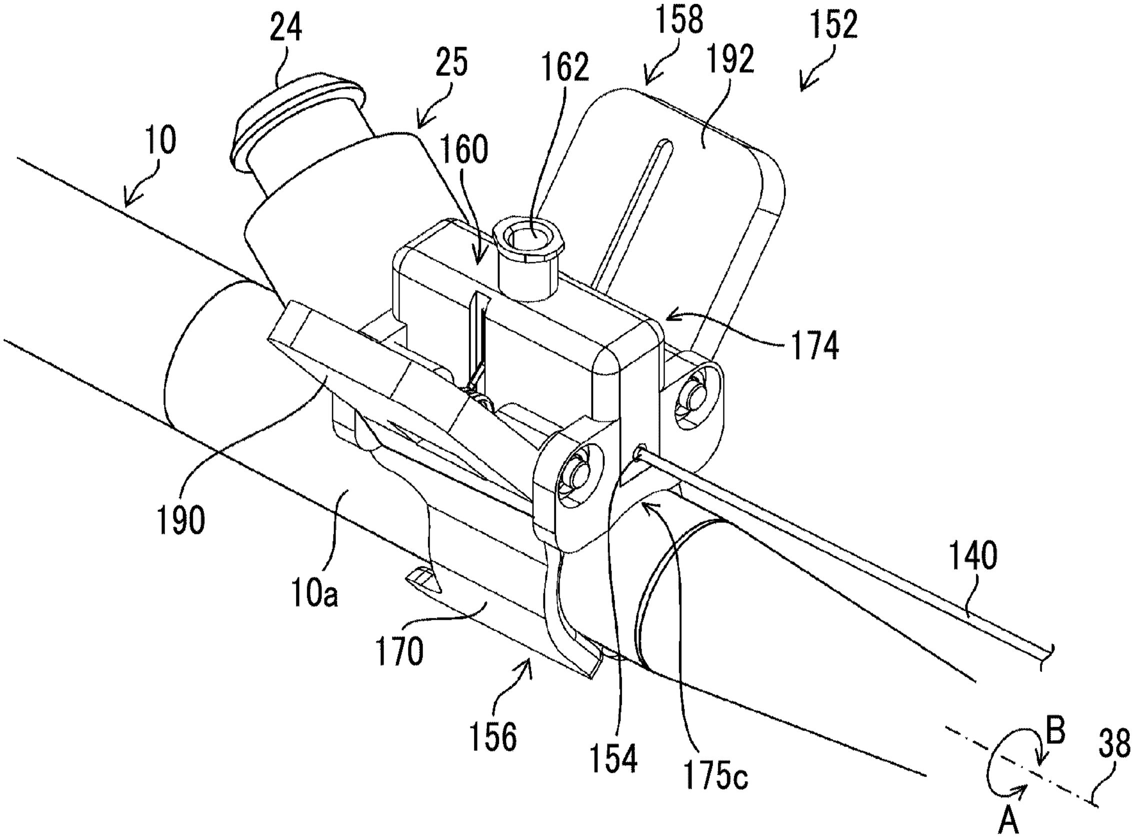
FIG. 18 is a perspective view of the fixing portion viewed from a distal end side of the operating portion.

FIG. 16 is an assembly perspective view showing a configuration of the fixing portion 152. Each of FIGS. 17 and 18 is a perspective view showing a state in which the fixing portion 152 is fixed to the operating portion 10. FIG. 17 is a perspective view of the fixing portion 152 as viewed from a proximal end side of the operating portion 10, and FIG. 18 is a perspective view of the fixing portion 152 as viewed from a distal end side of the operating portion 10.

As shown in FIGS. 16 to 18, the fixing portion 152 includes a grip member 156 that is attachably and detachably gripped and fixed to the operating portion 10, a knob member 158 that operates to hold or release a fixed state (gripping state) of the grip member 156 to the operating portion 10, and a port portion 160 that supplies and discharges an ultrasonic wave transmission medium to and from the tube 140. The knob member 158 is an example of an operation member of the embodiment of the present invention and is an operation member that operates to hold and release a fixed state of the fixing portion 152 (grip member 156) to the operating portion 10.

The port portion 160 has a supply/discharge port 162. A syringe 164 for supplying and discharging the ultrasonic wave transmission medium is connected to the supply/discharge port 162 through a tube 166 and a connector 168.

Figure 19:
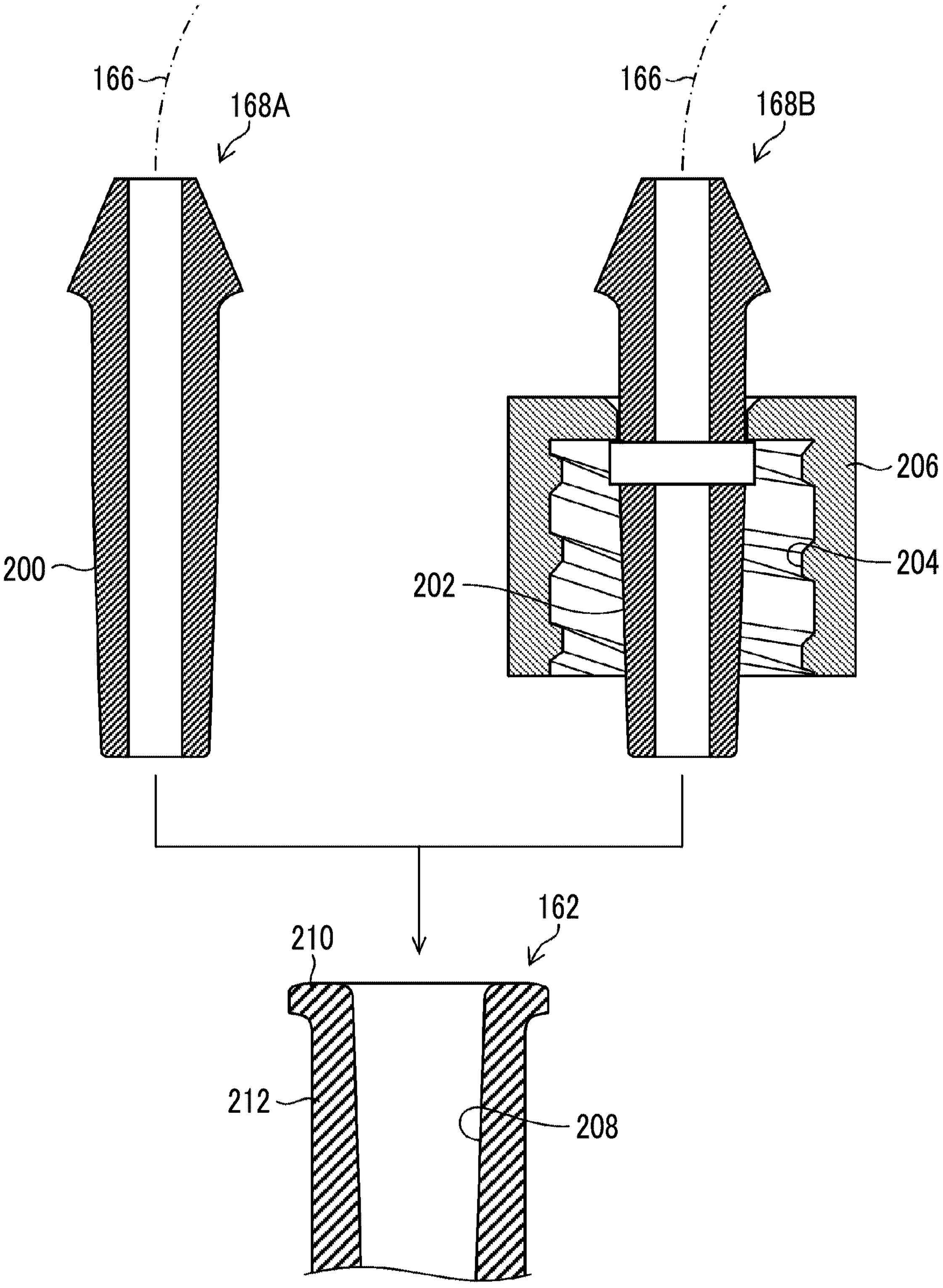
FIG. 19 is a sectional view showing an example of a luer taper type fitting.

FIG. 19 is a sectional view showing an example of a luer taper type fitting that connects the supply/discharge port 162 and the connector 168. The luer taper type fitting has two types of fittings such as a fitting type (luer slip type) and a screw type (luer lock type). In FIG. 19, a fitting type connector 168A is shown on a left side, and a screw type connector 168B is shown on a right side as the connector 168. The fitting type connector 168A has a nozzle portion 200 in which an outer peripheral surface is formed in a tapered shape. The screw type connector 168B has a nozzle portion 202 in which an outer peripheral surface is formed in a tapered shape, and a color portion 206 in which a female screw 204 is formed on an inner peripheral surface.

Meanwhile, the supply/discharge port 162 is configured in a shape (connection shape) corresponding to a luer lock connector, that is, the supply/discharge port 162 has a female fitting portion 212 in which a tapered hole 208 and a male screw portion 210 protruding outward in a radial direction are formed at a distal end part.

The supply/discharge port 162 and the fitting type connector 168A are bonded to each other by fitting the nozzle portion 200 into the tapered hole 208 of the female fitting portion 212. The supply/discharge port 162 and the screw type connector 168B are bonded to each other by fitting the nozzle portion 202 into the tapered hole 208 of the female fitting portion 212 and then rotating the color portion 206. As a result, the supply/discharge port 162 and the connectors 168A and 168B are connected to each other.

By configuring the supply/discharge port 162 as the luer lock connector in this way, the supply/discharge port 162 can be easily connected to the fitting type connector 168A or the screw type connector 168B. As a result, the ultrasonic wave transmission medium can be supplied and discharged through the supply/discharge port 162. In addition, by employing the luer taper type fitting, it is possible to reliably prevent the ultrasonic wave transmission medium from leaking from a connection portion between the supply/discharge port 162 and the connector 168 at the time of supplying and discharging the ultrasonic wave transmission medium.

The port portion 160 and the supply/discharge port 162 are examples of a port portion and a supply/discharge port of the embodiment of the present invention. In a case where the syringe 164 is directly connected to the supply/discharge port 162 without using the tube 166 and the connector 168, a distal end pipe 165 of the syringe 164 may be configured as the above-described fitting-type or screw-type connector.

As shown in FIGS. 15 and 16, the grip member 156 has a pair of grip bodies 170 and 172 facing each other. The grip bodies 170 and 172 are configured in a symmetrical shape and have clamping pieces 170*a* and 172*a* facing each other. The clamping pieces 170*a* and 172*a* are formed in a recessed shape that expands outward in an arc shape, and can grip (clamp) an arc-shaped outer peripheral surface 10*a* of the operating portion 10 in a radial direction of the operating portion 10. The pair of grip bodies 170 and 172 are examples of a pair of grip bodies of the embodiment of the present invention.

In addition, the pair of grip bodies 170 and 172 that configure the grip member 156 have a rubber sheet 173 having an anti-slip function on a portion that comes into contact with the operating portion 10. The rubber sheet 173 is attached to inner side surfaces of the clamping pieces 170*a* and 172*a* facing each other. The rubber sheet 173 is an example of an anti-slip member of the embodiment of the present invention.

The fixing portion 152 has a connecting member 174 that rotatably connects the pair of grip bodies 170 and 172 to each other. Hereinafter, a specific configuration will be described.

The connecting member 174 has a pair of shafts 176 and 178 that are disposed to be parallel to each other. Both ends of each of the shafts 176 and 178 are supported by bearing portions 180*a*, 180*b*, 182*a*, and 182*b* formed in the connecting member 174. In addition, the shafts 176 and 178 are prevented from falling off from the bearing portions 180*a*, 180*b*, 182*a*, and 182*b* (connecting members 174) by E-rings 184 that are mounted on the bearing portions 180*a*, 180*b*, 182*a*, and 182*b*, respectively.

The grip bodies 170 and 172 have tubular bearing portions 170*b* and 172*b* consecutively provided at the clamping pieces 170*a* and 172*a*, respectively. The shafts 176 and 178 are inserted into and disposed in the bearing portions 170*b* and 172*b*. Accordingly, the grip bodies 170 and 172 are rotatably connected to the connecting member 174 through the shafts 176 and 178, respectively. As a result, the grip bodies 170 and 172 (clamping pieces 170*a* and 172*a*) can clamp the outer peripheral surface 10*a* of the operating portion 10 in the radial direction of the operating portion 10. The connecting member 174 is an example of a connecting member of the embodiment of the present invention.

Further, the fixing portion 152 has torsion springs 186 and 188. The shafts 176 and 178 are inserted into coil portions 186*a* and 188*a* of the torsion springs 186 and 188. Accordingly, the torsion springs 186 and 188 are attached to the connecting member 174 through the shafts 176 and 178.

The torsion springs 186 and 188 have locking pins 186*b*, 186*c*, 188*b*, and 188*c* at both end portions of the coil portions 186*a* and 188*a*, respectively. The locking pins 186*b* and 188*b* are locked to grooves 174*a* and 174*b* formed in the connecting member 174, respectively, and the locking pins 186*c* and 188*c* are locked to a knob member 158 to be described below.

Figure 20:
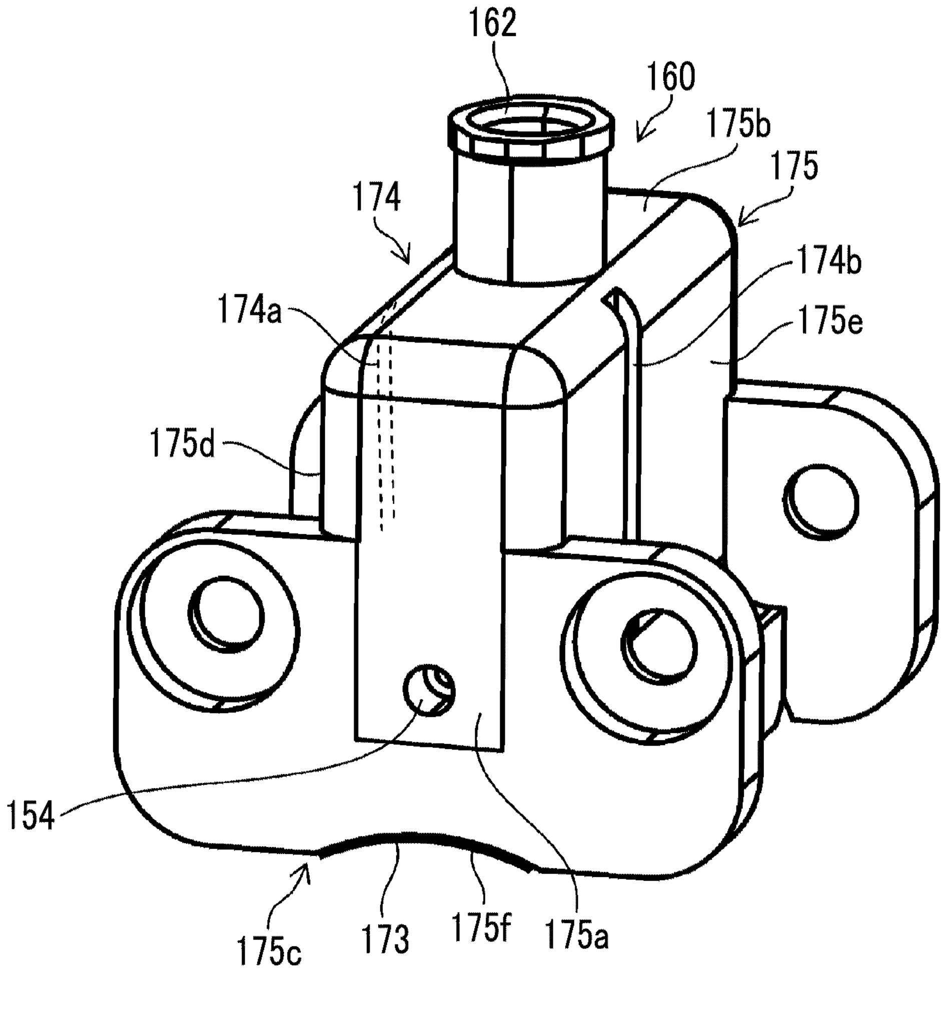
FIG. 20 is an enlarged perspective view of a connecting member.

The connecting member 174 will be described in detail. FIG. 20 is an enlarged view of the connecting member 174 shown in FIG. 16. As shown in FIG. 20, the connecting member 174 has a connecting body portion 175. An outer shape of the connecting body portion 175 is configured in a substantially rectangular parallelepiped shape. In addition, in a case where the connecting body portion 175 is viewed from the distal end side of the operating portion 10 (see FIG. 18), the connecting body portion 175 has a front surface 175*a*, an outer side surface 175*b*, an inner side surface 175*c*, a left side surface 175*d*, and a right side surface 175*e*. The hole portion 154 described above is formed on the front surface 175*a*. In addition, the groove 174*a* and the groove 174*b* described above are formed on the left side surface 175*d* and the right side surface 175*e*.

Returning to FIG. 16, the knob member 158 has a pair of knob bodies 190 and 192. The knob bodies 190 and 192 are consecutively provided at the clamping pieces 170*a* and 172*a* through the bearing portions 170*b* and 172*b*, respectively. That is, the knob member 158 is integrally formed with the grip member 156. In addition, the locking pins 186*c* and 188*c* of the torsion springs 186 and 188 described above are locked to the grooves 190*a* and 192*a* formed in the knob bodies 190 and 192, respectively.

Accordingly, in a case where the pair of knob bodies 190 and 192 are operated by fingers of a practitioner in a direction in which the pair of knob bodies 190 and 192 approach each other, the pair of grip bodies 170 and 172 are rotated in a direction (a direction toward the outside in the radial direction of the operating portion 10) in which the pair of grip bodies 170 and 172 are separated from each other against biasing forces of the torsion springs 186 and 188. In addition, in a case where the fingers are separated from the pair of knob bodies 190 and 192, the pair of grip bodies 170 and 172 are rotated in a direction (a direction toward the inside in the radial direction of the operating portion 10) in which the pair of grip bodies 170 and 172 approach each other by means of the biasing forces of the torsion springs 186 and 188. Grip force is applied to the grip member 156 by this operation, and the fixing portion 152 is fixed to the operating portion 10. The torsion springs 186 and 188 are examples of a grip force applying member of the embodiment of the present invention.

In a case where the fixing portion 152 is fixed to the operating portion 10, the inner side surface 175*c* of the connecting body portion 175 shown in FIG. 20 functions as a surface for gripping (clamping) the operating portion 10 in cooperation with each of the inner side surfaces (the rubber sheet 173) of the grip bodies 170 and 172. In addition, in a case where the grip bodies 170 and 172 grip the operating portion 10, the inner side surface 175*c* has a shape that avoids a protrusion portion of the operating portion 10. Hereinafter, a specific configuration will be described.

In the present example, a forceps introduction portion 25 (see FIGS. 17 and 18) of the treatment tool inlet port 24 is exemplified as the above-described protrusion portion. The forceps introduction portion 25 is a substantially cylindrical member that protrudes from an outer peripheral surface of the operating portion 10 toward the proximal end side of the operating portion 10. The inner side surface 175*c* of the connecting body portion 175 has an arc-shaped recess portion 175*f* that avoids an arc-shaped outer peripheral surface 25*a* of the forceps introduction portion 25. The rubber sheet 173 is also attached to the recess portion 175*f*. In addition, the treatment tool inlet port 24 corresponds to a forceps sleeve.

FIGS. 17 and 18 show a fixing form in which the recess portion 175*f* of the inner side surface 175*c* is engaged to the outer peripheral surface 25*a* while avoiding the outer peripheral surface 25*a* of the forceps introduction portion 25. At this time, the grip bodies 170 and 172 grip the outer peripheral surface 10*a* of the operating portion 10 excluding the forceps introduction portion 25. The connecting member 174 is provided with such a recess portion 175*f*, whereby it is possible to position the fixing portion 152 in the forceps introduction portion 25, and to fix the fixing portion 152 to the forceps introduction portion 25 in a state where rotation is restrained.

Next, the function of the grip member 156 (grip bodies 170 and 172) will be described. The grip member 156 has the following functions in addition to the function of gripping the outer peripheral surface 10*a* of the operating portion 10 excluding the forceps introduction portion 25.

That is, in some cases, the practitioner may operate the endoscope 1 by gripping the operating portion 10 with a left hand or by gripping the operating portion 10 with a right hand. In this case, depending on a fixing position of the fixing portion 152 with respect to the operating portion 10, the tube 166 (or the syringe 164 directly connected to the port portion 160) that is drawn from the port portion 160 may be an obstacle for the practitioner or may hinder the operability of the endoscope 1.

Therefore, in order to improve the operability of the endoscope 1, it is required that a direction to which the port portion 160 faces (a direction to which the tube 166 is drawn from the port portion 160 or a direction to which the syringe 164 directly connected to the port portion 160 faces) can be changed in accordance with the preference of the practitioner. In addition, even in a case where the direction to which the port portion 160 faces is changed, it is required that the fixing portion 152 can be positioned on the operating portion 10 and can be fixed in a state where the rotation is restrained.

Therefore, the fixing portion 152 of the present example comprises the grip member 156, whereby the fixing portion 152 can be fixed to the operating portion 10 at any position. Accordingly, the direction to which the port portion 160 faces can be changed to a direction according to the preference of the practitioner.

Figure 21:
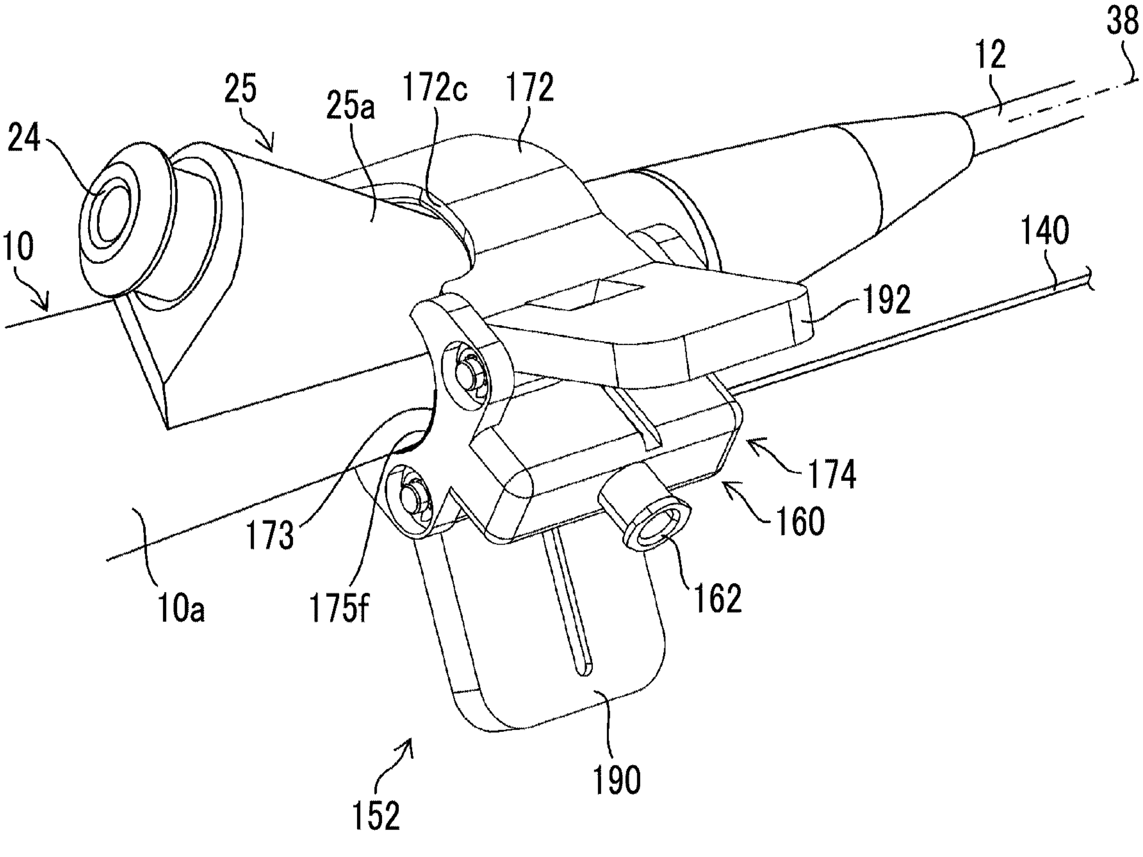
FIG. 21 is an explanatory view showing an example of a fixing form of the fixing portion to the operating portion.
Figure 22:
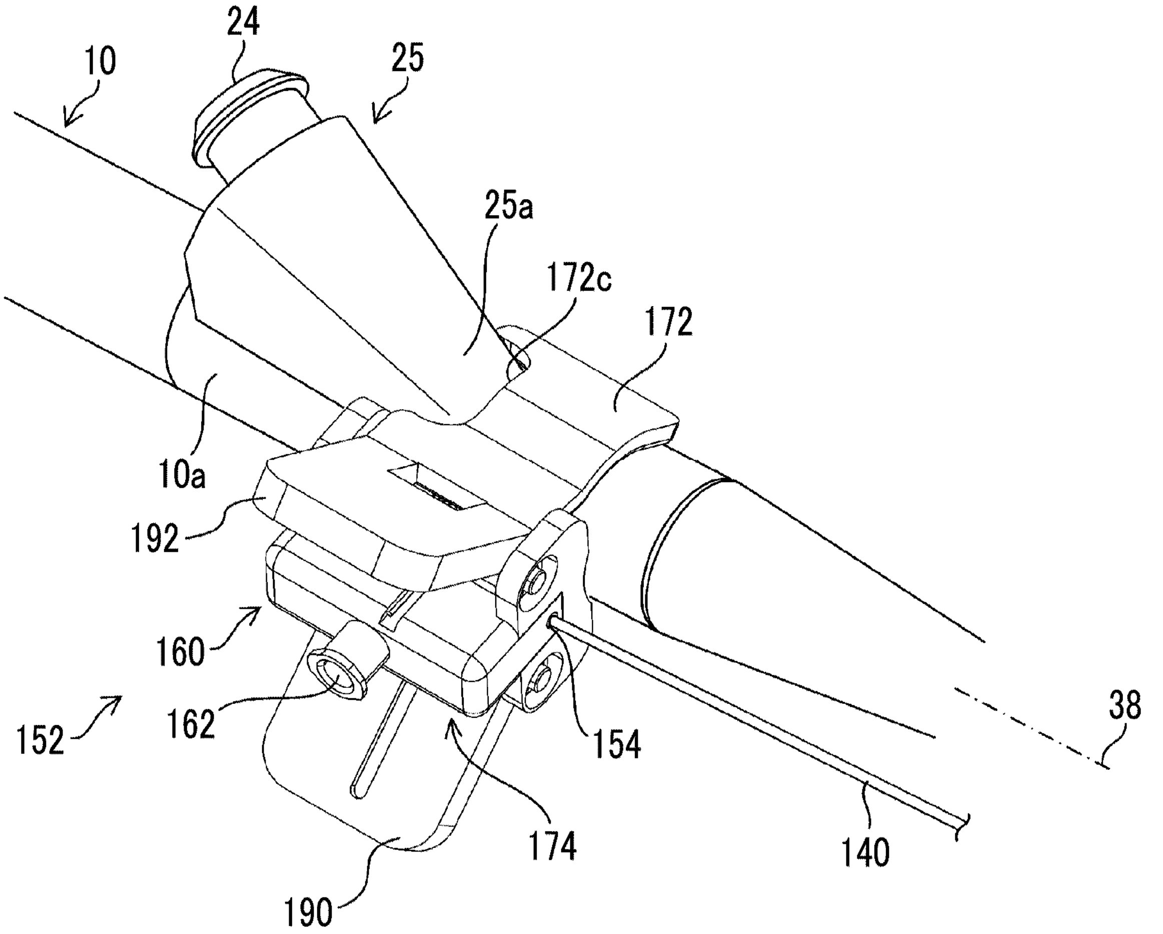
FIG. 22 is an explanatory view showing an example of the fixing form of the fixing portion to the operating portion.

Next, two fixing forms in a case where the direction to which the port portion 160 faces is changed will be described. FIGS. 21 and 22 show a configuration of a fixing form (hereinafter, referred to as a second fixing form) in which the fixing portion 152 is fixed by being shifted by about 90 degrees (counterclockwise direction as viewed from the distal end side of the operating portion 10) around a longitudinal axis 38 in a direction of an arrow A with respect to a fixing form of the fixing portion 152 (hereinafter, referred to as a first fixing form) shown in FIG. 18. That is, the second fixing form is a fixing form in which the direction to which the port portion 160 faces is inclined by about 90 degrees in the direction of the arrow A with respect to the first fixing form. Particularly, the second fixing form is a form that is easy to operate for the practitioner who grips the operating portion 10 with the left hand. FIG. 21 is a perspective view of the fixing portion 152 as viewed from the proximal end side of the operating portion 10, and FIG. 22 is a perspective view of the fixing portion 152 as viewed from the distal end side of the operating portion 10.

In the second fixing form, the grip body 172 (clamping piece 172*a*) of the grip bodies 170 and 172 facing the forceps introduction portion 25 is formed in a recessed shape as described above, whereby the grip body 172 (clamping piece 172*a*) is engaged to the outer peripheral surface 25*a* while avoiding the outer peripheral surface 25*a* of the forceps introduction portion 25. In addition, a recessed notched portion 172*c* facing a distal end side of the grip body 172 is formed on a proximal end side surface of the grip body 172, and the notched portion 172*c* is engaged to the outer peripheral surface 25*a* while avoiding the outer peripheral surface 25*a* of the forceps introduction portion 25 in the second fixing form. At this time, the recess portion 175*f* of the connecting body portion 175 and the other grip body 170 (clamping piece 170*a*) are engaged to the outer peripheral surface 10*a* while avoiding the outer peripheral surface 10*a* of the operating portion 10.

Figure 23:
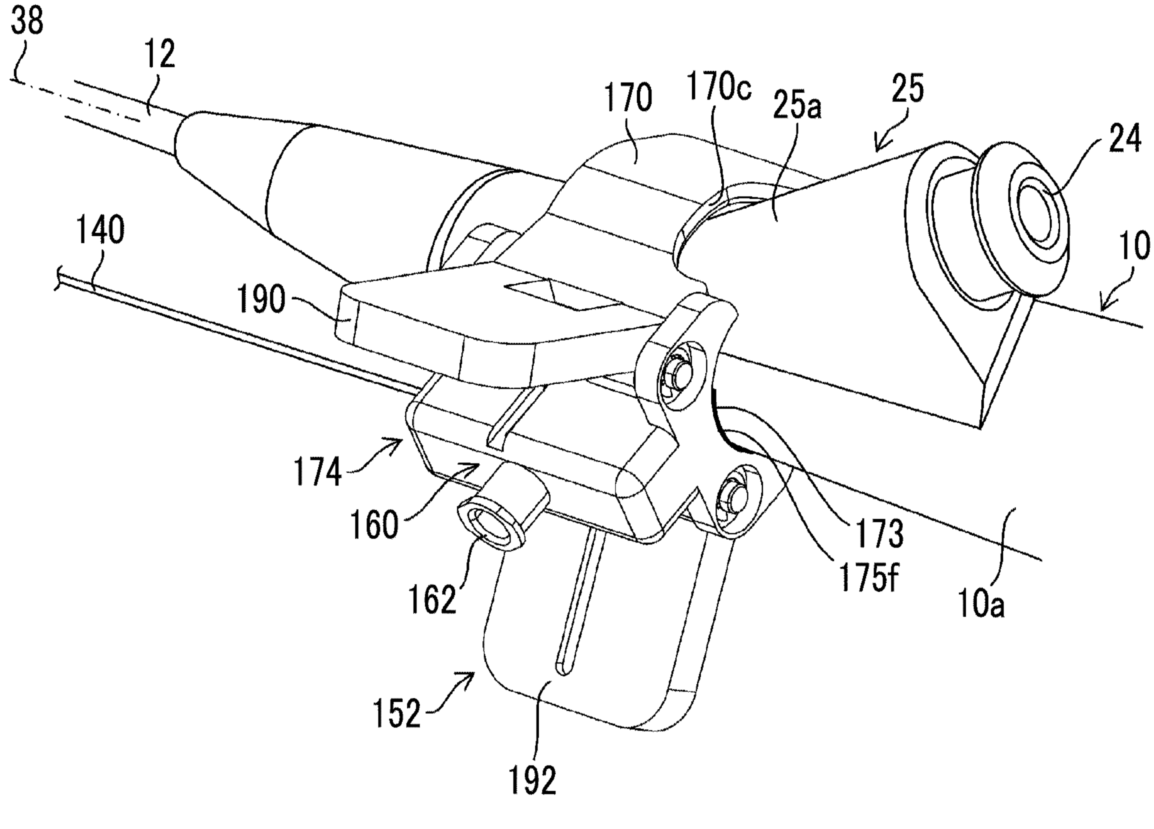
FIG. 23 is an explanatory view showing an example of the fixing form of the fixing portion to the operating portion.
Figure 24:
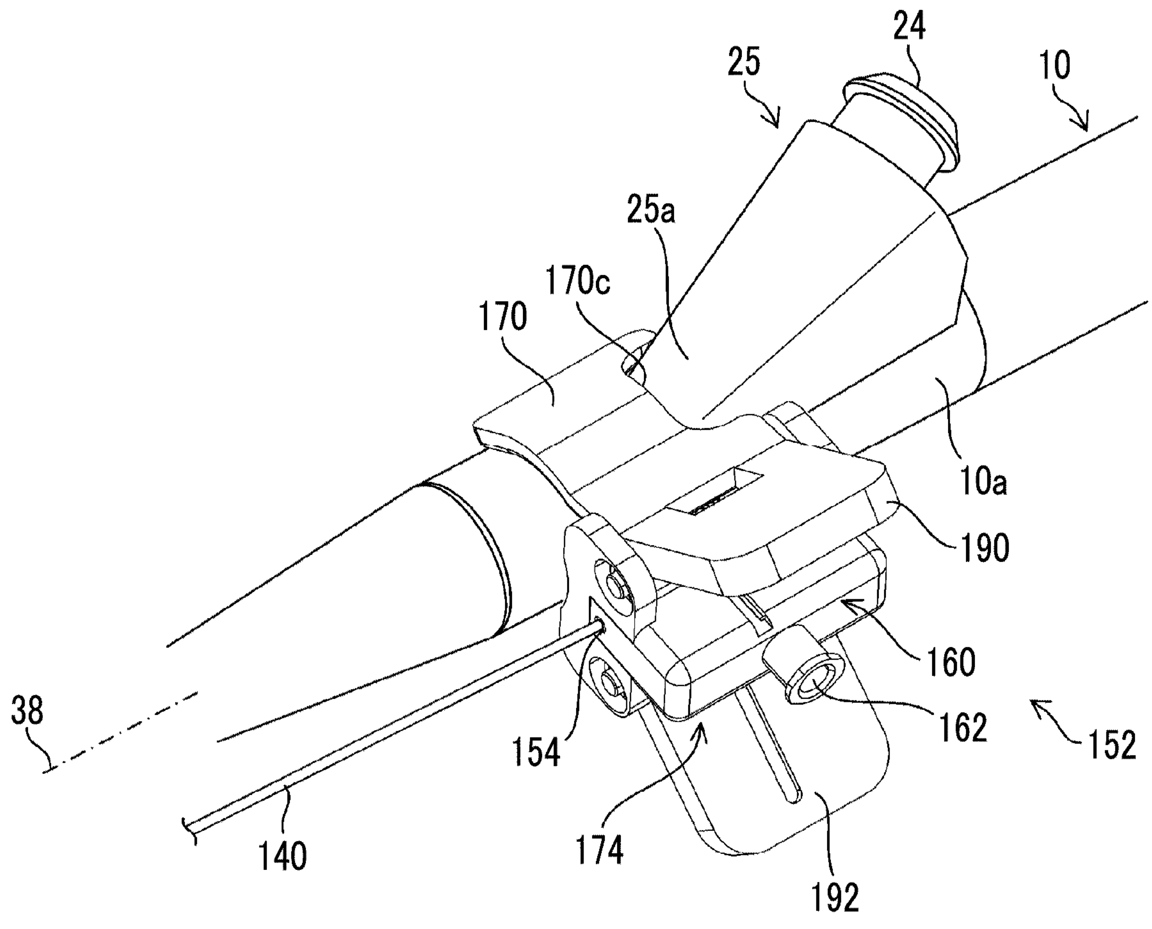
FIG. 24 is an explanatory view showing an example of the fixing form of the fixing portion to the operating portion.

Meanwhile, FIGS. 23 and 24 show a configuration of a fixing form (hereinafter, referred to as a third fixing form) in which the fixing portion 152 is fixed by being shifted by about 90 degrees around the longitudinal axis 38 in a direction of an arrow B (clockwise direction as viewed from the distal end side of the operating portion 10) with respect to the first fixing form. That is, the third fixing form is a fixing form in which the direction to which the port portion 160 faces is inclined by about 90 degrees in the direction of the arrow B with respect to the first fixing form. Particularly, the third fixing form is a form that is easy to operate for the practitioner who grips the operating portion 10 with the right hand. FIG. 23 is a perspective view of the fixing portion 152 as viewed from the proximal end side of the operating portion 10, and FIG. 24 is a perspective view of the fixing portion 152 as viewed from the distal end side of the operating portion 10.

In the third fixing form, the grip body 170 (clamping piece 170*a*) of the grip bodies 170 and 172 facing the forceps introduction portion 25 is formed in a recessed shape as described above, whereby the grip body 170 (clamping piece 170*a*) is engaged to the outer peripheral surface 25*a* while avoiding the outer peripheral surface 25*a* of the forceps introduction portion 25. In addition, a recessed notched portion 170*c* facing a distal end side of the grip body 170 is formed on a proximal end side surface of the grip body 170, and the notched portion 170*c* is engaged to the outer peripheral surface 25*a* while avoiding the outer peripheral surface 25*a* of the forceps introduction portion 25 in the third fixing form. At this time, the recess portion 175*f* of the connecting body portion 175 and the other grip body 172 (clamping piece 172*a*) are engaged to the outer peripheral surface 10*a* while avoiding the outer peripheral surface 10*a* of the operating portion 10.

As described above, the grip bodies 170 and 172 (the clamping pieces 170*a* and 172*a*) are formed in a shape that can be engaged to the outer peripheral surface 25*a* while avoiding the outer peripheral surface 25*a* (recessed shape), and the notched portions 170*c* and 172*c* are formed in the grip bodies 170 and 172 in a shape that can be engaged to the outer peripheral surfaces 25*a* (recessed shape) while avoiding the outer peripheral surface 25*a*. Thus, even in a case where the direction to which the port portion 160 faces is adjusted to a direction according to the preference of the practitioner, the fixing portion 152 can be positioned on the forceps introduction portion 25, and the fixing portion 152 can be fixed to the forceps introduction portion 25 in a state where the rotation is restrained.

Figure 25:
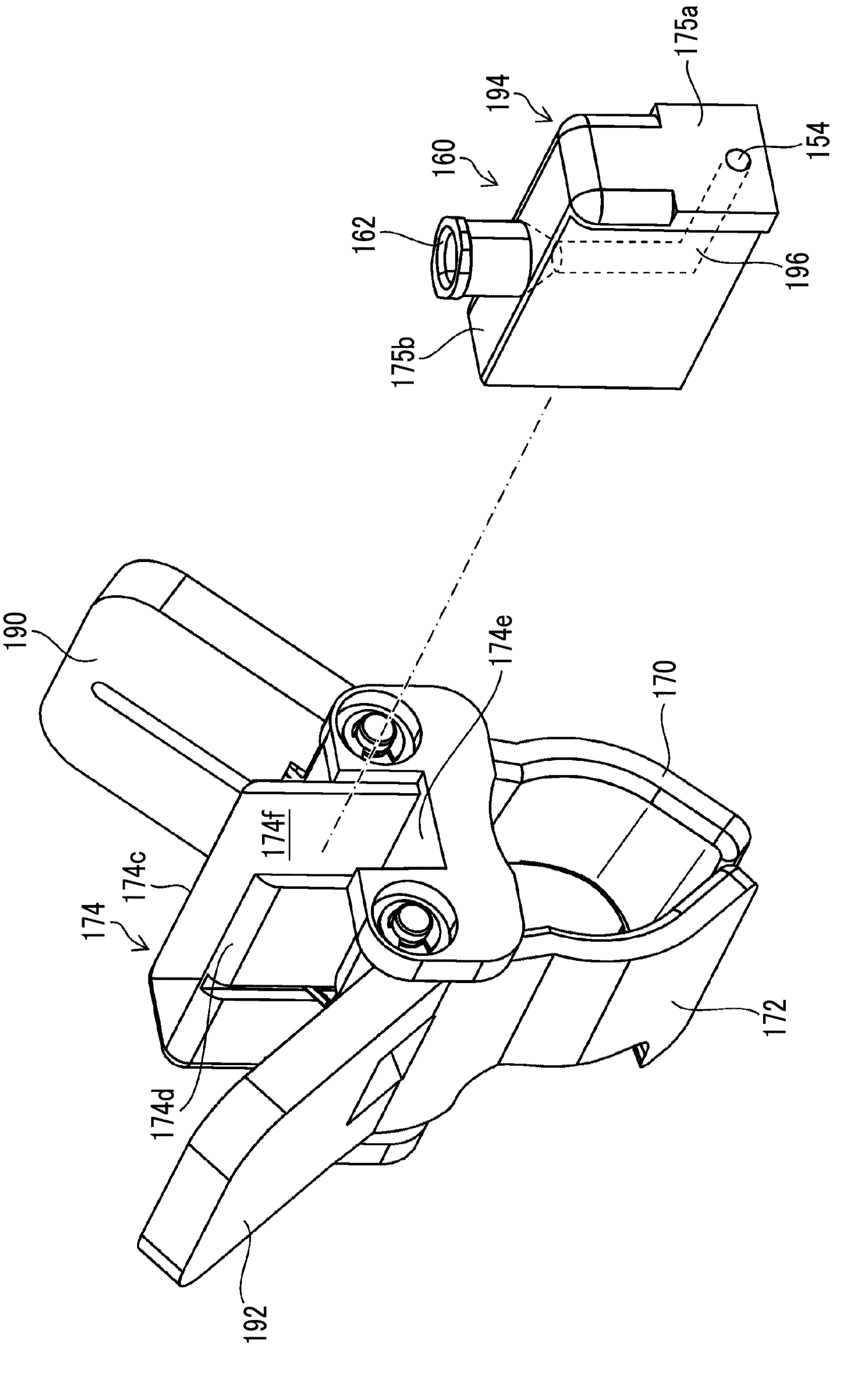
FIG. 25 is an explanatory view showing a configuration of a port portion.

FIG. 25 is a perspective view showing a state in which the port portion 160 is removed from the connecting member 174. As shown in FIG. 25, the port portion 160 of the present example is attachable to and detachable from the connecting member 174.

The port portion 160 has an attachment member 194 having a substantially rectangular parallelepiped shape. The attachment member 194 has a front surface 175*a* and an outer side surface 175*b* that are a part of the connecting body portion 175, a hole portion 154 is formed on the front surface 175*a*, and a supply/discharge port 162 is formed on the outer side surface 175*b*. In addition, the attachment member 194 has an L-shaped supply/discharge passage 196 that communicates with the hole portion 154 and the supply/discharge port 162 inside the attachment member 194.

The attachment member 194 configured as described above is attachably and detachably housed in a recessed accommodation groove 174*f* defined of a left side wall 174*c*, a right side wall 174*d*, and a bottom surface 174*e* of the connecting member 174. Accordingly, the port portion 160 is attachably and detachably attached to the connecting member 174.

Next, some effects of the ultrasonic wave transmission medium supply/discharge member 150 of the embodiment will be described.

Since the fixing portion 152 connected to the balloon 120 through the tube 140 in the ultrasonic wave transmission medium supply/discharge member 150 of the embodiment is configured to be attachably and detachably fixed to the operating portion 10, it is possible to prevent the tube 140 from being routed during the operation of the endoscope 1 by the practitioner. Therefore it is possible to improve operability of the endoscope 1.

Further, since the knob member 158 that is an operation member that operates to hold and release the fixed state of the fixing portion 152 to the operating portion 10 is provided in the fixing portion 152 constituting the ultrasonic wave transmission medium supply/discharge member 150 of the embodiment, the fixing portion 152 can be easily attached to and detached from the operating portion 10 by operating the operation member (knob member 158).

In the embodiment, the knob member 158 is shown as an example of the operation member according to the embodiment of the present invention, but the present invention is not limited thereto. The operation member may be a member that can operate to hold and release the fixed state of the fixing portion 152 to the operating portion 10. That is, the operation member of the embodiment of the present invention is not limited to a knob shape that can be pinched with a finger as in the knob member 158, and may have, for example, a hooked shape that can be hooked with a finger or other shapes.

In addition, in the embodiment, the configuration has been shown in which the fixing portion 152 comprises the grip member 156 (the pair of grip bodies 170 and 172) that is attachably and detachably gripped and fixed to the operating portion 10, but the embodiment is not limited thereto, and the configuration is sufficient as long as the fixing portion 152 is attachably and detachably fixed to the operating portion 10. For example, the fixing portion 152 may comprise an engaging member, an adsorption member, a magnet, or the like, and the fixing portion 152 may be fixed to the operating portion 10 by engagement, adsorption, magnetic force, or the like.

In addition, in the ultrasonic wave transmission medium supply/discharge member 150 of the embodiment, the fixing portion 152 can be fixed to the operating portion 10 at a position according to the preference of the practitioner. Thus, the direction to which the port portion 160 faces can be changed according to the preference of the practitioner.

The port portion 160 is provided with the supply/discharge port 162, whereby a supply/discharge unit such as the syringe 164 can be connected to the supply/discharge port 162. As a result, it is possible to easily supply and discharge the ultrasonic wave transmission medium to and from the balloon 120.

In addition, the pair of grip bodies 170 and 172 are rotatably provided on the connecting member 174, whereby it is possible to easily fix the fixing portion 152 to the operating portion 10.

In addition, the connecting member 174 is provided with the port portion 160, for example, whereby a supply/discharge unit such as the syringe 164 can be connected to the port portion 160 (supply/discharge port 162) without interfering with the operation of the knob member 158.

Further, the fixing portion 152 is provided with the torsion springs 186 and 188, whereby grip force can be applied to the pair of grip bodies 170 and 172. Accordingly, the fixing portion 152 can be reliably fixed to the operating portion 10.

In addition, since the fixing portion 152 comprises the recess portion 175*f* and the grip bodies 170 and 172 (clamping pieces 170*a* and 172*a*) having shapes that can be engaged while avoiding the forceps introduction portion 25, the fixing portion 152 can be positioned on the forceps introduction portion 25. Further, it is possible to fix the fixing portion 152 to the forceps introduction portion 25 in a state where the rotation is restrained. Further, the fixing position of the fixing portion 152 with respect to the operating portion 10 can be easily ascertained.

In addition, since the grip bodies 170 and 172 (clamping pieces 170*a* and 172*a*) are provided with the rubber sheet 173, it is possible to prevent misalignment of the fixing portion 152 caused by slip with respect to the operating portion 10. Further, since the rubber sheet 173 is also provided for the recess portion 175*f*, it is possible to more reliably prevent the above-mentioned misalignment.

In addition, the supply/discharge port 162 has a shape that can be connected to the luer lock connector, whereby the supply and discharge of the ultrasonic wave transmission medium can be performed through the luer lock connector.

In addition, since the port portion 160 is attachable to and detachable from the connecting member 174, the port portion 160 can be made disposable. Accordingly, it is unnecessary to clean and sterilize the port portion 160 (particularly, the hole portion 154, the supply/discharge port 162, and the supply/discharge passage 196).

The fixing portion 152 in which the pair of grip bodies 170 and 172 are rotatably connected to the connecting member 174 has been described in the embodiment, but the embodiment is not limited thereto. For example, even a fixing portion having a configuration in which the pair of grip bodies 170 and 172 are rotatably connected to each other through one shaft without using the connecting member 174 can be applied.

In the embodiment, although an example in which the fixing portion 152 is fixed to the forceps introduction portion 25 (protrusion portion) has been described, the embodiment is not limited thereto. For example, the fixing portion 152 can be fixed even on a flat outer peripheral surface 10*a*, excluding the forceps introduction portion 25, out of the outer peripheral surface 10*a* of the operating portion 10.

Although the ultrasonic wave transmission medium supply/discharge member and the endoscope system according to the embodiment have been described above, some improvements or modifications may be made to the present invention without departing from the gist of the present invention.

EXPLANATION OF REFERENCES

1: ultrasonic endoscope
10: operating portion

10*a*: outer peripheral surface
12: insertion portion
14: universal cord
16: angle lever
22: suction button
23: treatment tool insertion channel
24: treatment tool inlet port
25: forceps introduction portion
25*a*: outer peripheral surface
30: soft part
32: bendable part
34: distal end part body
34*a*: ultrasonic attachment portion
34*b*: outlet port forming portion
34*c*: body portion
34*d*: inclined surface
38: longitudinal axis
40: observation optical system
40*a*: observation window
40*b*: lens system
40*c*: imaging element
44: illumination optical system
44*a*: illumination window
50: ultrasound transducer
51: oscillator surface
52: treatment tool outlet port
54: signal cable
56: signal cable
58: light guide
71: opening forming surface
74: pipe line
82: optical system storage portion
84: convex surface
85: stepped surface
91: standing wall portion
92: groove portion
93: plane portion
94: stepped portion
100: puncture needle
120: balloon for ultrasonic endoscope
120: balloon
121: balloon body
121*a*: storage portion
121*b*: adhesion portion
121*c*: adhesion region
122: inner portion
122*a*: opening portion
122*b*: side surface portion
122*c*: top surface portion
122*d*: inclined surface portion
122*e*: bottom surface portion
122*f*: first side surface portion
122*g*: second side surface portion
122*h*: stepped portion
122*i*: flange portion
122*j*: protrusion portion
122*k*: locking portion
122*m*: communication path
122*n*: tapered portion
122*p*: tapered portion
122*q*: flat portion
124: outer portion
124*a*: opening portion
124*b*: side surface portion
124*c*: top surface portion
124*d*: inclined surface portion
124*e*: bottom surface portion
124*f*: oscillator surface region
124*g*: thick portion
124*h*: transition portion
124*i*: recess portion
140: tube
140*a*: distal end opening portion
140*b*: proximal end opening portion
150: ultrasonic wave transmission medium supply/discharge member
152: fixing portion
154: hole portion
156: grip member
158: knob member
160: port portion
162: supply/discharge port
164: syringe
166: tube
168: connector
168A: connector
168B: connector
170: grip body
170*a*: clamping piece
170*b*: bearing portion
170*c*: notched portion
172: grip body
172*a*: clamping piece
172*b*: bearing portion
172*c*: notched portion
173: rubber sheet
174: connecting member
174*a*: groove
174*b*: groove
174*c*: left side wall
174*d*: right side wall
174*e*: bottom surface
174*f*: accommodation groove
175: connecting body portion
175*a*: front surface
175*b*: outer side surface
175*c*: inner side surface
175*d*: left side surface
175*e*: right side surface
175*f*: recess portion
176: shaft
178: shaft
180*a*: bearing portion
180*b*: bearing portion
182*a*: bearing portion
182*b*: bearing portion
184: E-ring
186: torsion spring
188: torsion spring
186*a*: coil portion
186*b*: locking pin
186*c*: locking pin
188*a*: coil portion
188*b*: locking pin
188*c*: locking pin
190: knob body
190*a*: groove
192: knob body
192*a*: groove
194: attachment member
196: supply/discharge passage
200: nozzle portion
202: nozzle portion
204: female screw

206: color portion
208: tapered hole
210: male screw portion
212: female fitting portion

What is claimed is:

1. An ultrasonic wave transmission medium supply/discharge member comprising:

a balloon for an ultrasonic endoscope that is mounted to cover an outer surface of an ultrasound transducer provided in a distal end part body on a distal end side of an insertion portion of an ultrasonic endoscope, wherein the balloon for an ultrasonic endoscope has a storage portion that is configured to be filled with an ultrasonic wave transmission medium, a tube that communicates with an inside of the storage portion, and a fixing portion that is configured to be attachably and detachably fixed to an operating portion provided at a proximal end of the ultrasonic endoscope, wherein the tube is connected between the fixing portion and the storage portion of the balloon, such that the fixing portion is connected to the balloon for an ultrasonic endoscope through the tube.

2. The ultrasonic wave transmission medium supply/discharge member according to claim 1, wherein the fixing portion has an operation member that operates to hold and release a fixed state of the fixing portion to the operating portion.

3. The ultrasonic wave transmission medium supply/discharge member according to claim 1, wherein the fixing portion has a port portion that supplies and discharges the ultrasonic wave transmission medium into and from the tube.

4. The ultrasonic wave transmission medium supply/discharge member according to claim 3, wherein the port portion has a supply/discharge port to which a supply/discharge unit for supplying and discharging the ultrasonic wave transmission medium is connectable.

5. The ultrasonic wave transmission medium supply/discharge member according to claim 4, wherein the supply/discharge port has a shape that is connectable with a luer lock connector.

6. The ultrasonic wave transmission medium supply/discharge member according to claim 4, wherein the supply/discharge port is configured to supply and discharge the ultrasonic wave transmission medium through a luer lock connector.

7. The ultrasonic wave transmission medium supply/discharge member according to claim 1, wherein the fixing portion has a pair of grip bodies facing each other, and a connecting member that rotatably connects the pair of grip bodies to each other.

8. The ultrasonic wave transmission medium supply/discharge member according to claim 7, wherein the connecting member has a port portion that supplies and discharges the ultrasonic wave transmission medium into and from the tube.

9. The ultrasonic wave transmission medium supply/discharge member according to claim 8, wherein the port portion has a structure that is attachable to and detachable from the connecting member.

10. The ultrasonic wave transmission medium supply/discharge member according to claim 7, wherein the fixing portion has a grip force applying member that applies grip force of the pair of grip bodies.

11. The ultrasonic wave transmission medium supply/discharge member according to claim 1, wherein the fixing portion has a shape that is engageable with a part of a protrusion portion included in the operating portion while avoiding another part of the protrusion portion included in the operating portion.

12. The ultrasonic wave transmission medium supply/discharge member according to claim 11, wherein the protrusion portion is a forceps introduction portion of a forceps sleeve provided in the operating portion.

13. The ultrasonic wave transmission medium supply/discharge member according to claim 1, wherein the fixing portion has an anti-slip member at a portion that comes into contact with the operating portion.

14. An endoscope system comprising:

the ultrasonic wave transmission medium supply/discharge member according to claim 1; and an ultrasonic endoscope including an operating portion that is provided at a proximal end thereof and configured to be attachably and detachably fixed to the fixing portion.

15. The endoscope system according to claim 14, wherein the operating portion has a protrusion portion that is engageable with the fixing portion.

16. The endoscope system according to claim 15, wherein the protrusion portion is a forceps introduction portion of a forceps sleeve provided in the operating portion.

* * * * *